United States Patent
Vahey

(10) Patent No.: US 9,594,027 B2
(45) Date of Patent: Mar. 14, 2017

(54) APPARATUS AND METHOD FOR SPECTROSCOPIC ANALYSIS OF RESIDUE

(71) Applicant: The Boeing Company, Chicago, IL (US)

(72) Inventor: Paul G. Vahey, Seattle, WA (US)

(73) Assignee: The Boeing Company, Chicago, IL (US)

( * ) Notice: Subject to any disclaimer, the term of this patent is extended or adjusted under 35 U.S.C. 154(b) by 271 days.

(21) Appl. No.: 14/290,085

(22) Filed: May 29, 2014

(65) Prior Publication Data

US 2015/0346110 A1 Dec. 3, 2015

(51) Int. Cl.
| | |
|---|---|
| *G01N 21/01* | (2006.01) |
| *G01N 21/94* | (2006.01) |
| *G01J 3/10* | (2006.01) |
| *G01J 1/42* | (2006.01) |
| *G01J 3/42* | (2006.01) |
| *G01J 3/02* | (2006.01) |

(52) U.S. Cl.
CPC ............ *G01N 21/94* (2013.01); *G01J 1/4204* (2013.01); *G01J 3/0208* (2013.01); *G01J 3/0218* (2013.01); *G01J 3/0262* (2013.01); *G01J 3/10* (2013.01); *G01J 3/42* (2013.01); *G01N 2201/061* (2013.01)

(58) Field of Classification Search
CPC . G01N 21/94; G01N 2201/061; G01J 1/4204; G01J 3/0208; G01J 3/0218; G01J 3/0262; G01J 3/10; G01J 3/42

USPC ....................................................... 356/244
See application file for complete search history.

(56) References Cited

U.S. PATENT DOCUMENTS

| | | | | |
|---|---|---|---|---|
| 2004/0219531 | A1* | 11/2004 | DiCesare | B01L 3/5085 435/6.13 |
| 2005/0275837 | A1* | 12/2005 | Zhang | B82Y 30/00 356/301 |
| 2008/0220441 | A1* | 9/2008 | Birnbaum | G01N 33/566 435/7.1 |
| 2010/0277742 | A1* | 11/2010 | McMillan | G01N 15/1463 356/450 |
| 2012/0202709 | A1* | 8/2012 | Bergo | C40B 30/10 506/12 |

OTHER PUBLICATIONS

"μFocus Sample Plates for MALDI-TOF MS," Hudson Surface Technology, www.maldiplate.com (2014).
Mozharov et al., "Effect of solid substrates on reproducibility of LIBS measurements," Applied Physics Laboratory, University of Washington (2013).

* cited by examiner

*Primary Examiner* — Sunghee Y Gray
(74) *Attorney, Agent, or Firm* — Walters & Wasylyna LLC

(57) ABSTRACT

One example of the present disclosure relates to an apparatus for spectroscopic analysis of residue. The apparatus includes a surface including a hydrophobic portion and a hydrophilic portion. The hydrophobic portion surrounds the hydrophilic portion. The hydrophilic portion includes a dimension equal to or larger than a width of a first incident non-destructive electromagnetic beam.

28 Claims, 19 Drawing Sheets

US 9,594,027 B2

APPARATUS AND METHOD FOR SPECTROSCOPIC ANALYSIS OF RESIDUE

BACKGROUND

Throughout various industries, such as aircraft manufacturing, residues and contamination on surfaces of various materials often need to be analyzed.

One available testing method for surface analysis is Matrix Assisted Laser Desorption-Ionization ("MALDI") mass-spectrometry analysis, wherein a sample is ablated, ionized, and then subjected to electric or magnetic fields. Since the ionized sample is destroyed in the process, archival of the sample and/or multiple measurements thereof are not possible. Furthermore, mass-spectrometry is bulky and expensive, which prevents on-site testing and, accordingly, increases the time and cost of material analysis.

Alternatively, non-destructive photo spectroscopy may be used to analyze surface contamination on the material. Trace levels of residue must often be extracted from the surface and concentrated by evaporating an extraction solvent before spectroscopic analysis. However, there are no reliable means to evenly deposit the residue on a surface that is compatible with spectroscopic analysis in a reproducible manner. Furthermore, traditional methods of infrared spectroscopy are not conducive to archiving the sample for subsequent measurements, since the sample is typically cleaned off of spectrometer window.

SUMMARY

Accordingly, apparatus and method, intended to address the above-identified concerns, would find utility.

One example of the present disclosure relates to an apparatus for spectroscopic analysis of residue. The apparatus includes a surface including a hydrophobic portion and a hydrophilic portion. The hydrophobic portion surrounds the hydrophilic portion. The hydrophilic portion includes a dimension equal to or larger than a width of a first incident non-destructive electromagnetic beam.

One example of the present disclosure relates to a method for analyzing a sample located on a hydrophilic portion of a surface. The method includes directing a first incident non-destructive electromagnetic beam through the sample at a non-zero incidence angle relative to the surface; and analyzing a first reflected non-destructive electromagnetic beam reflected from the hydrophilic portion to obtain a first measurement associated with at least one property of the sample.

BRIEF DESCRIPTION OF THE DRAWINGS

Figure 1A:
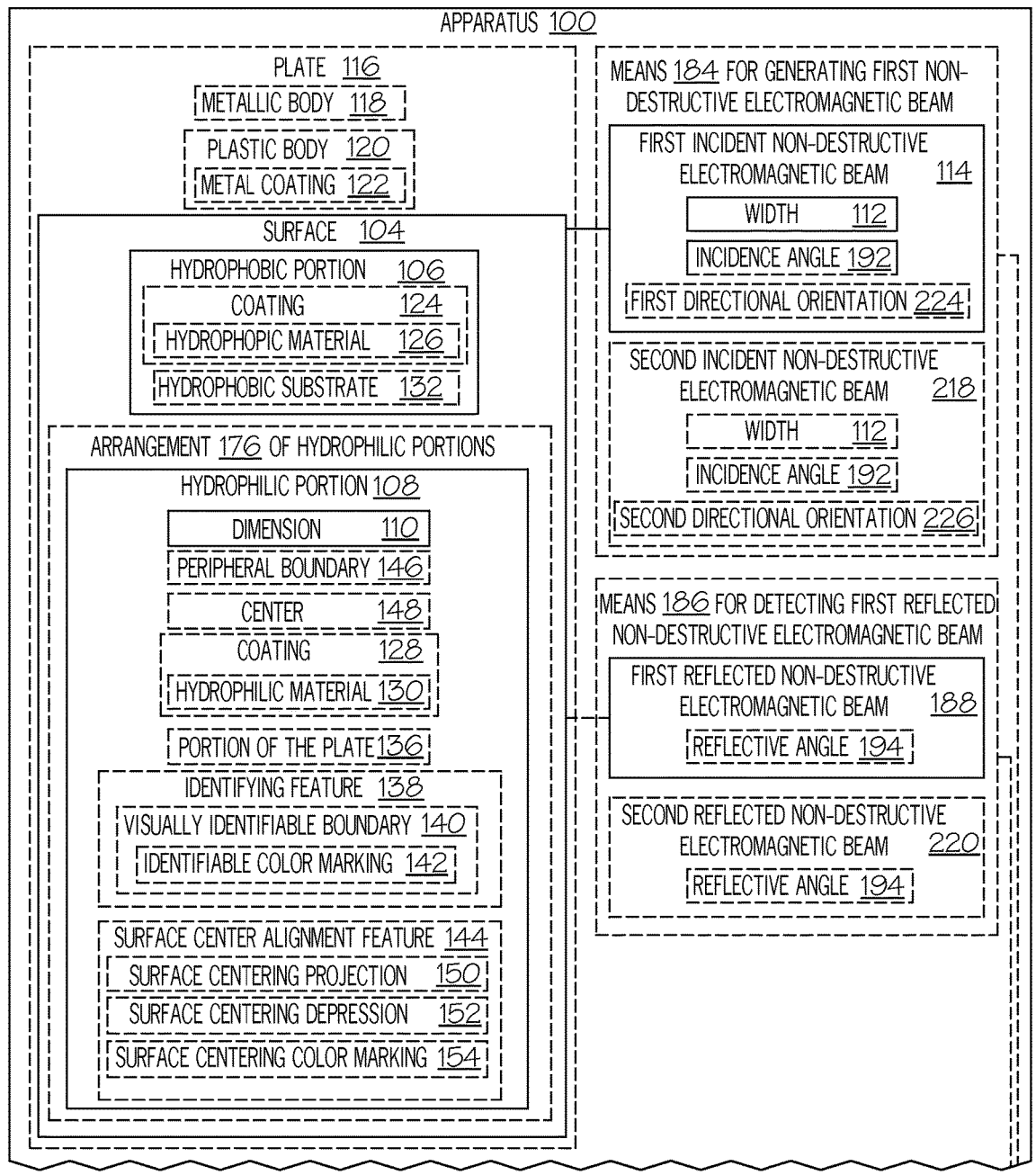
Figure 1B:
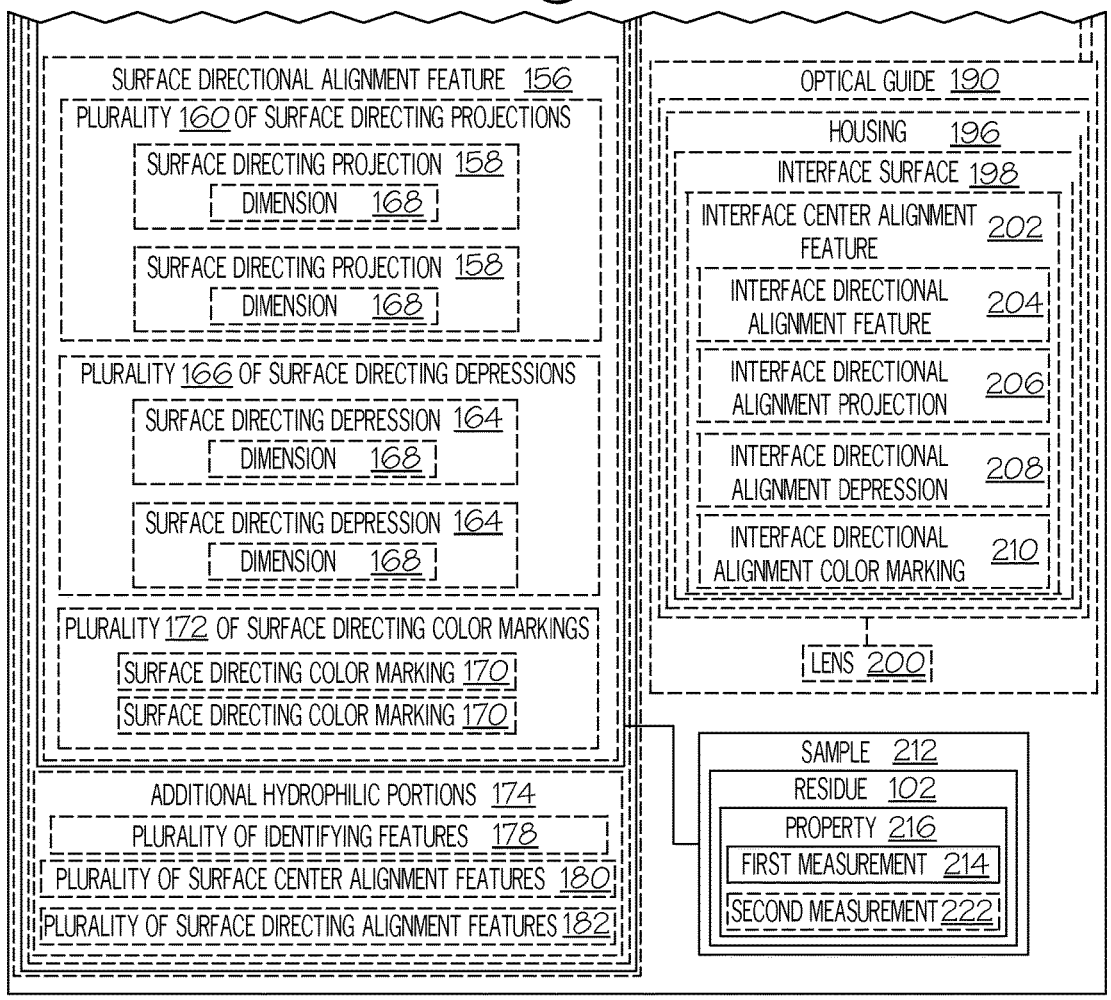
Figure 2:
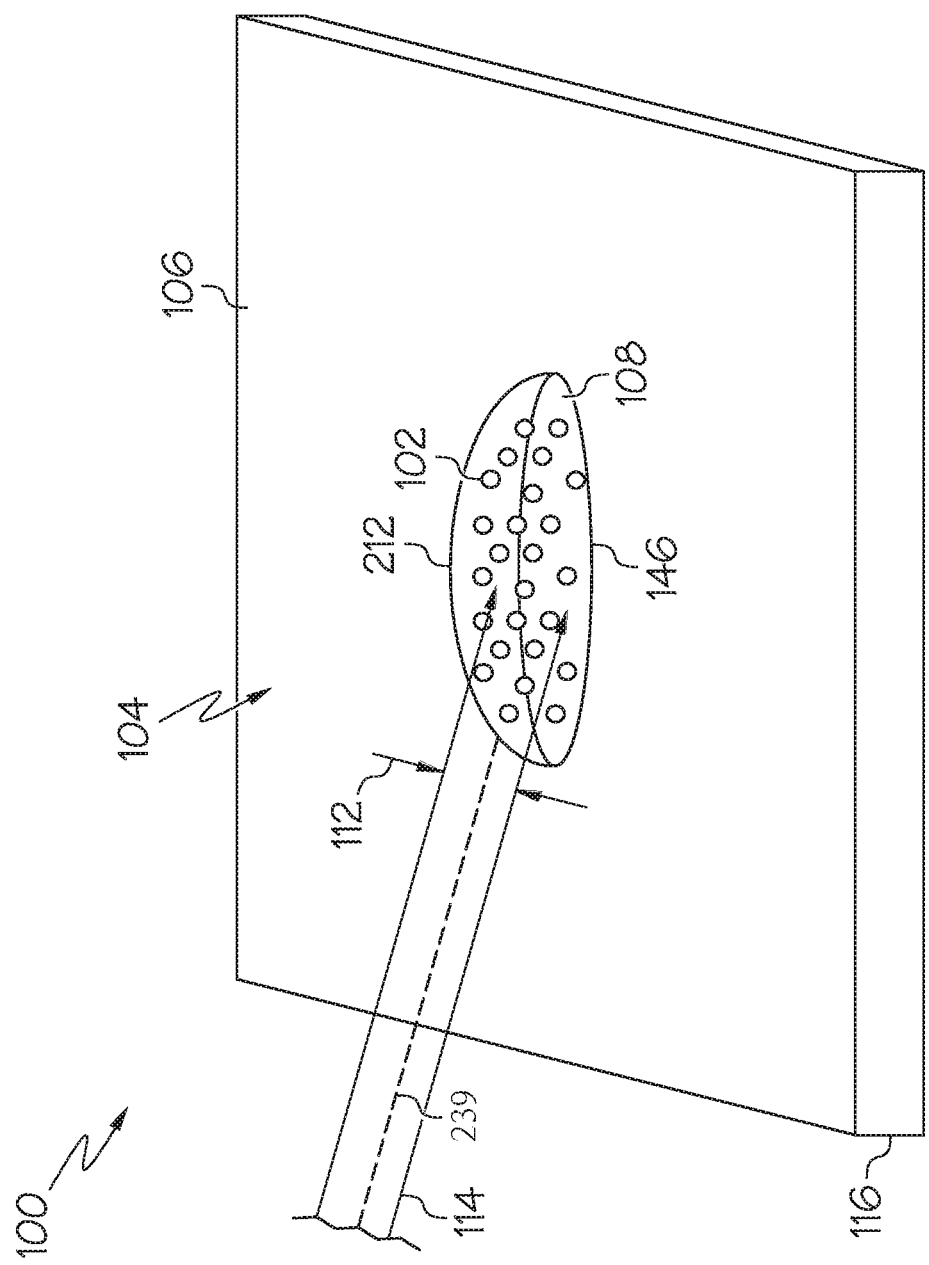
Figure 3:
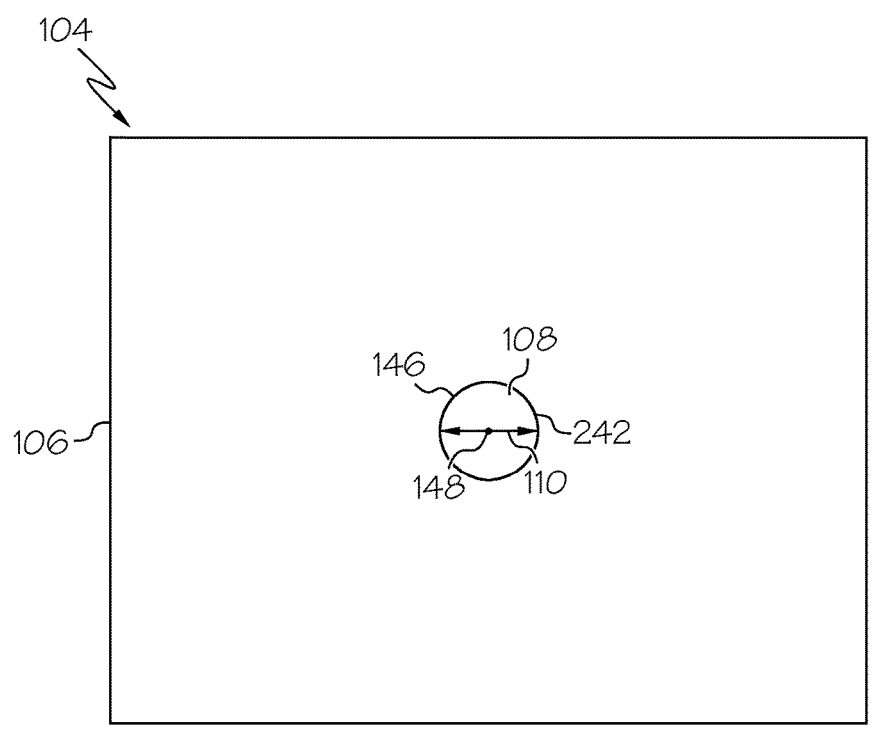
Figure 4:
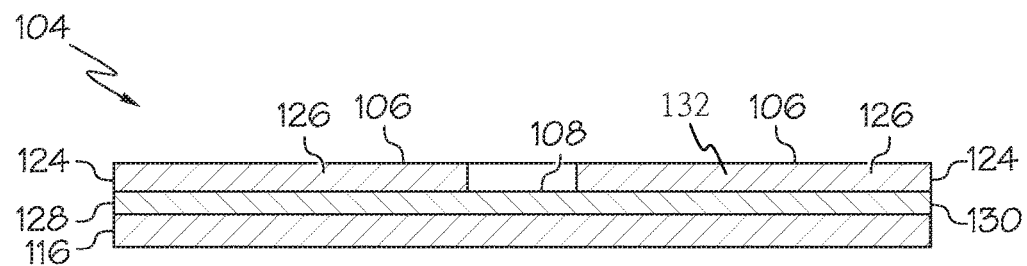
Figure 5:
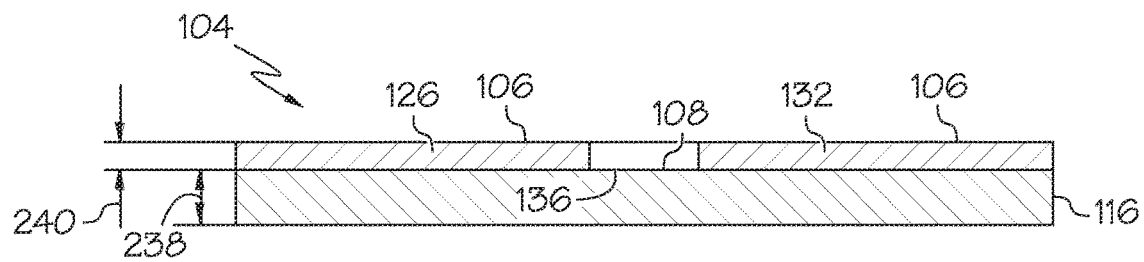
Figure 6:
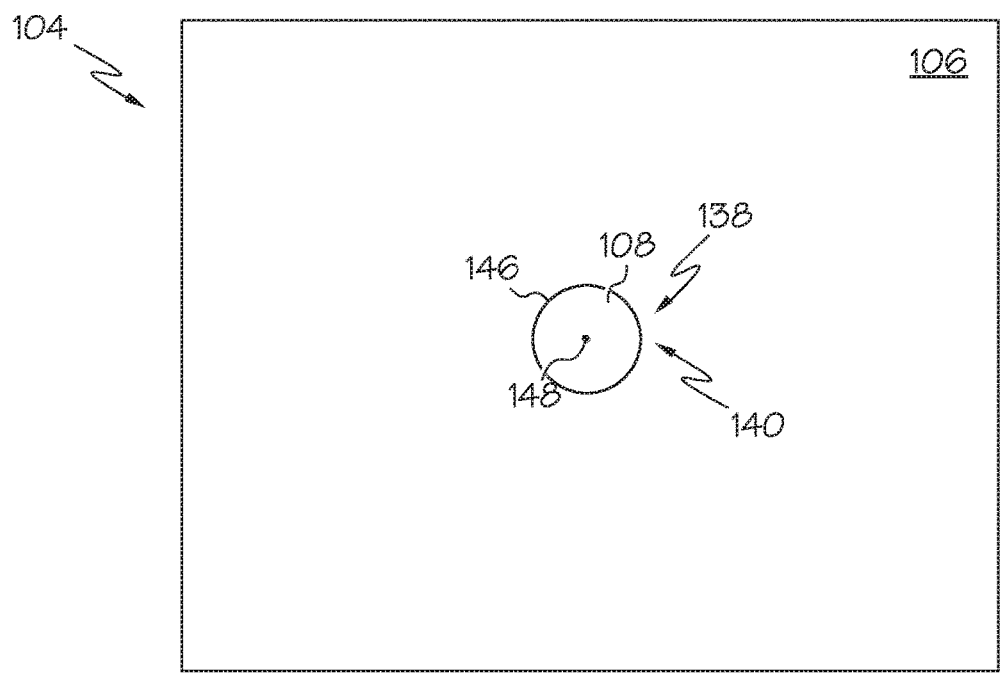
Figure 6A:
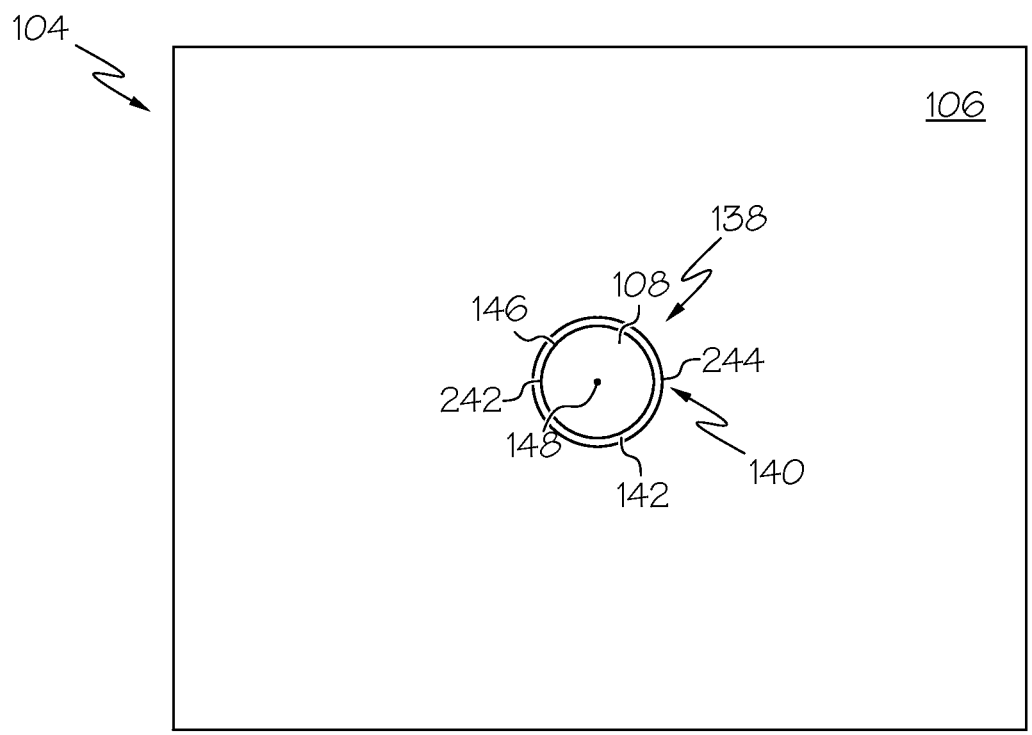
Figure 7:
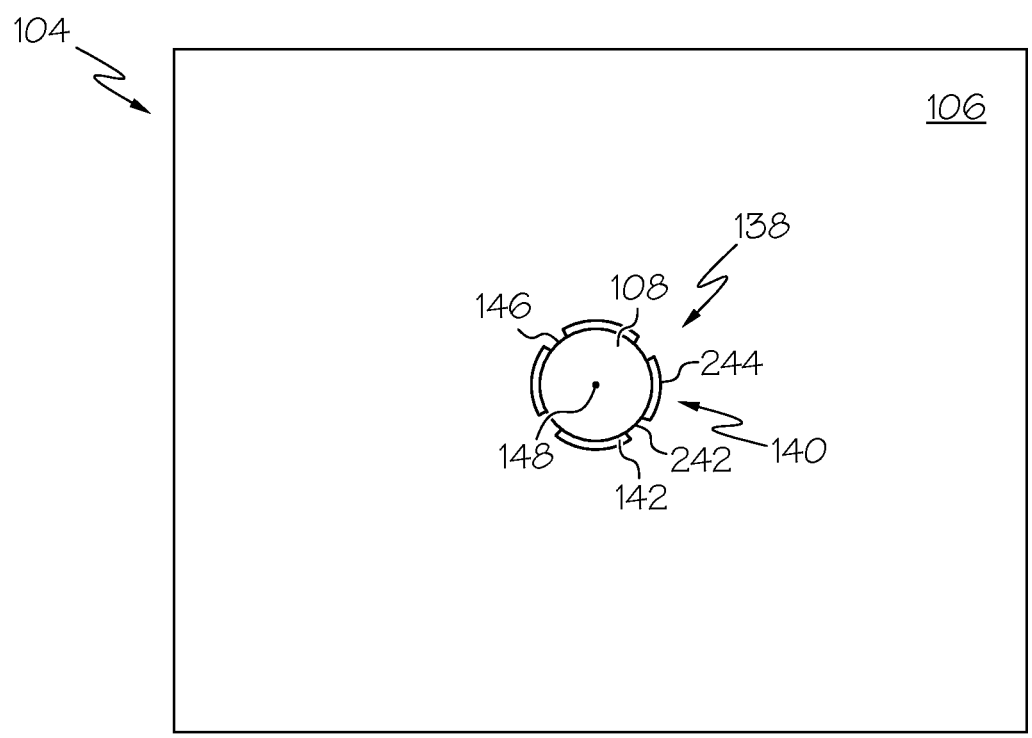
Figure 8:
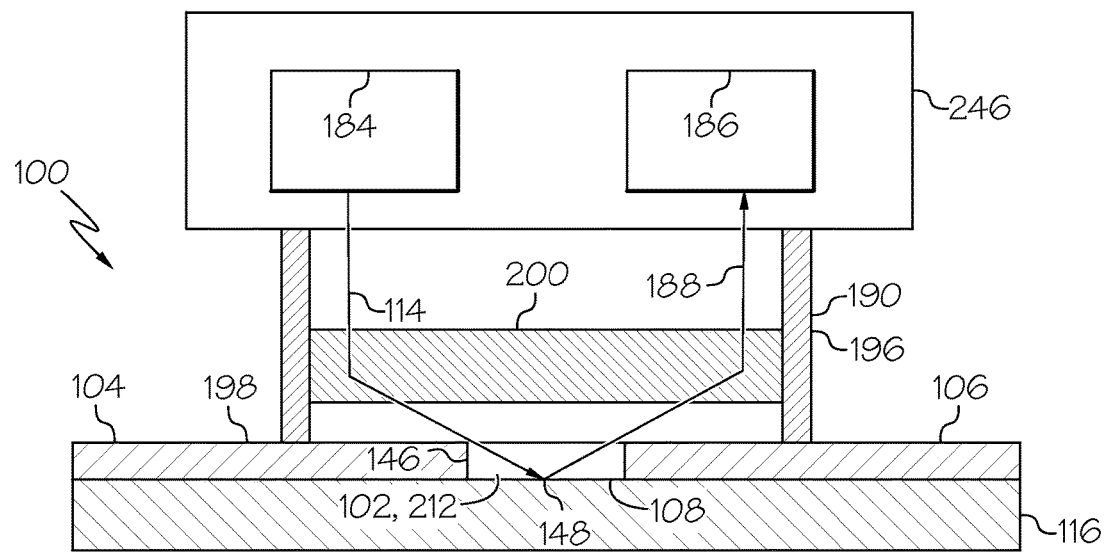
Figure 9:
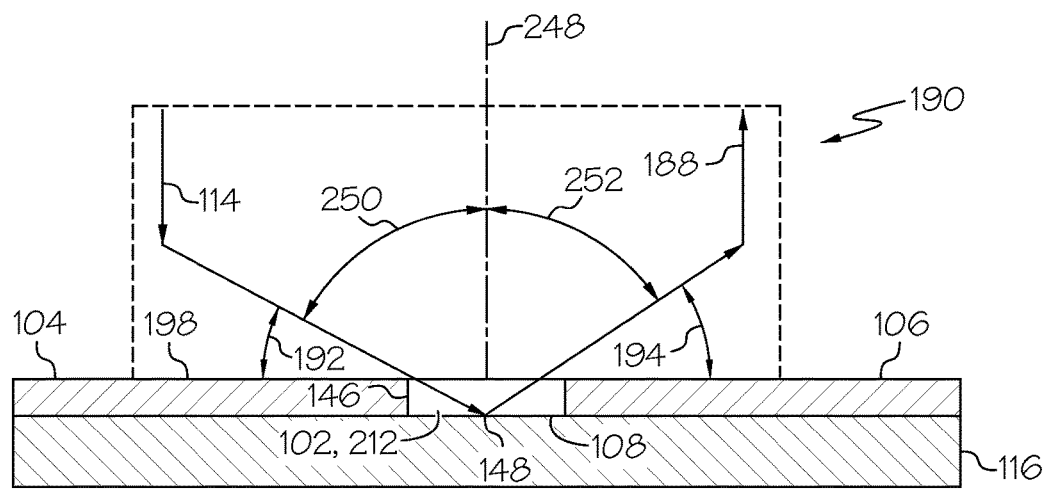
Figure 10:
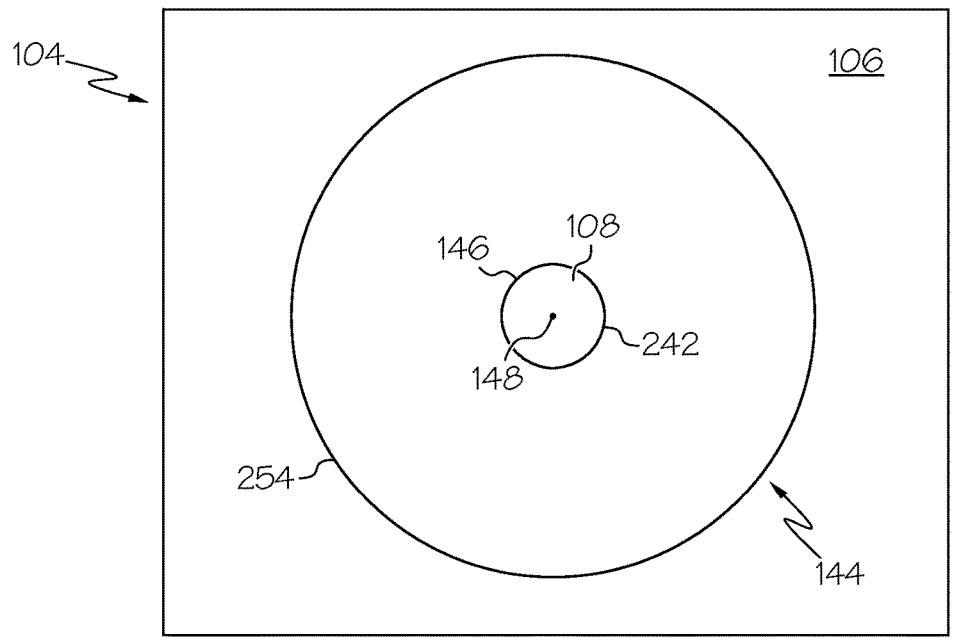
Figure 11:
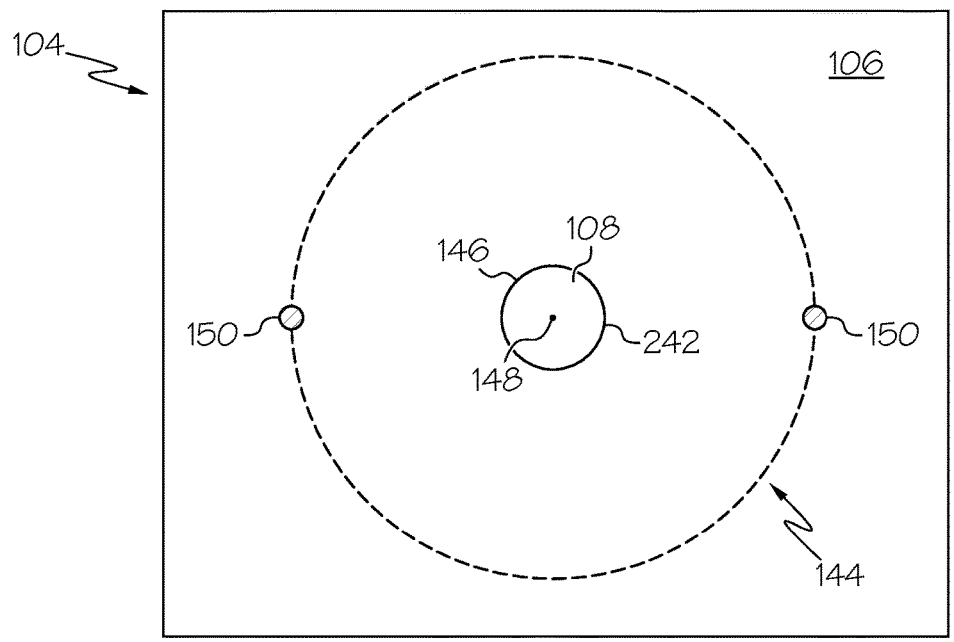
Figure 12:
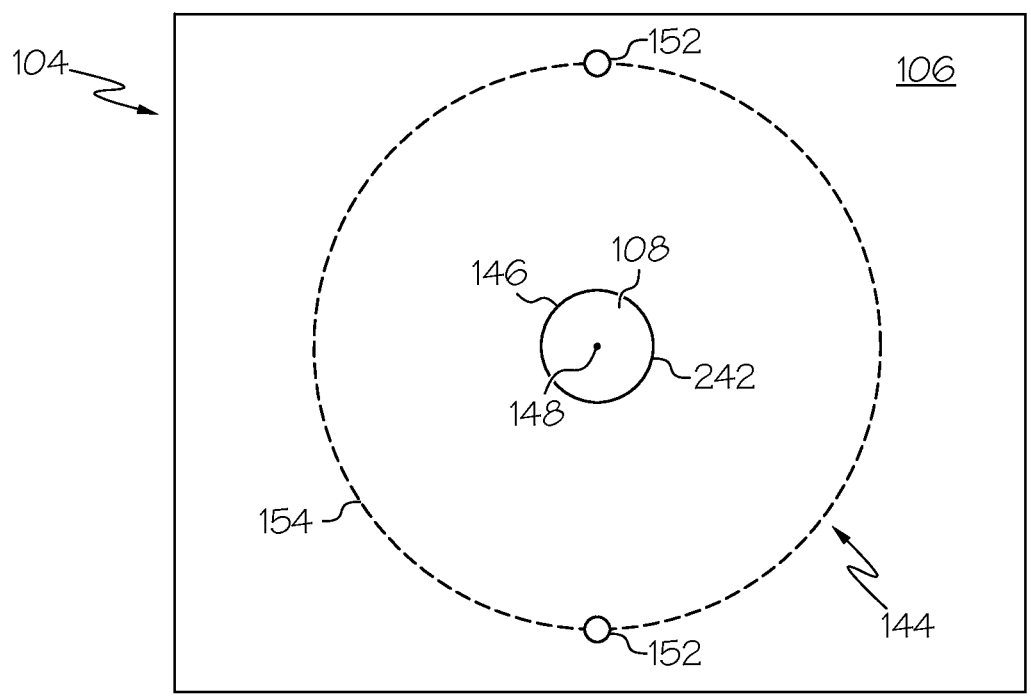
Figure 13:
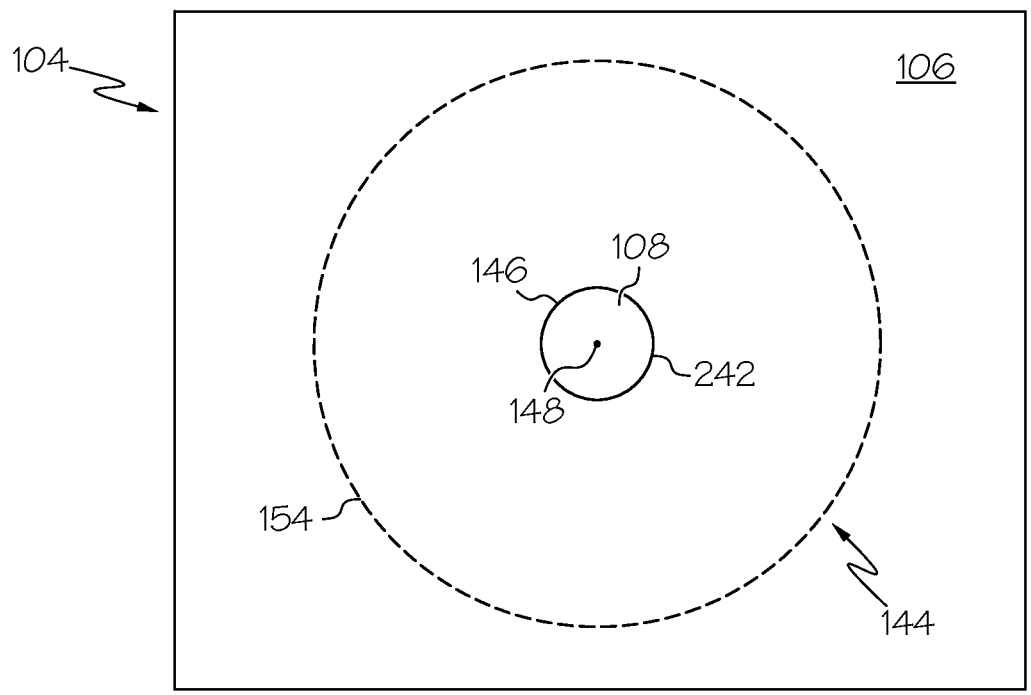
Figure 14:
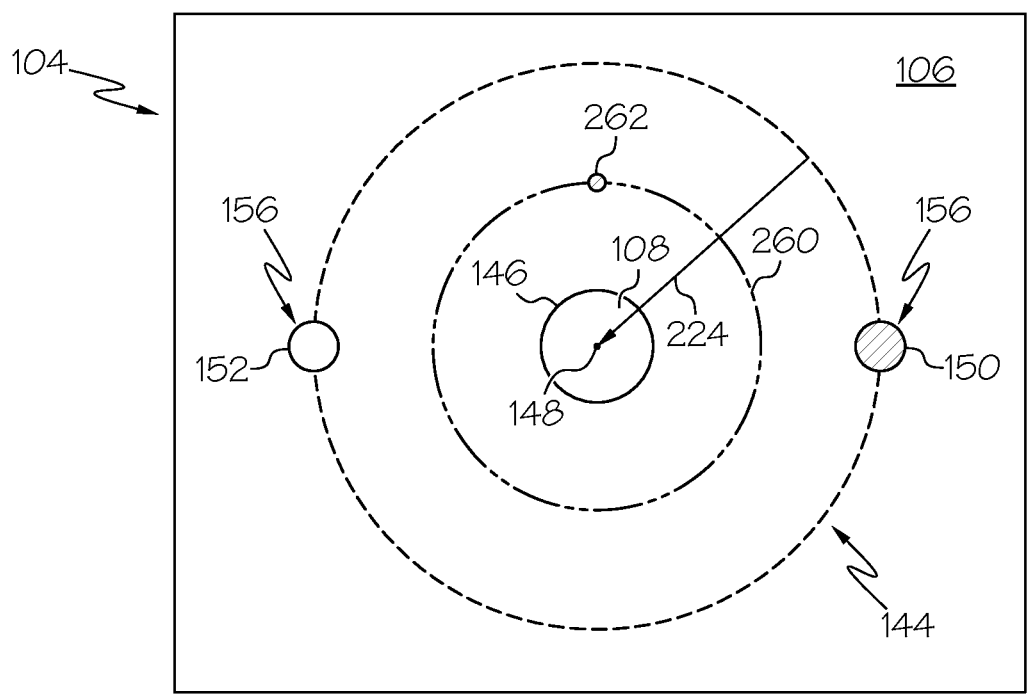
Figure 15:
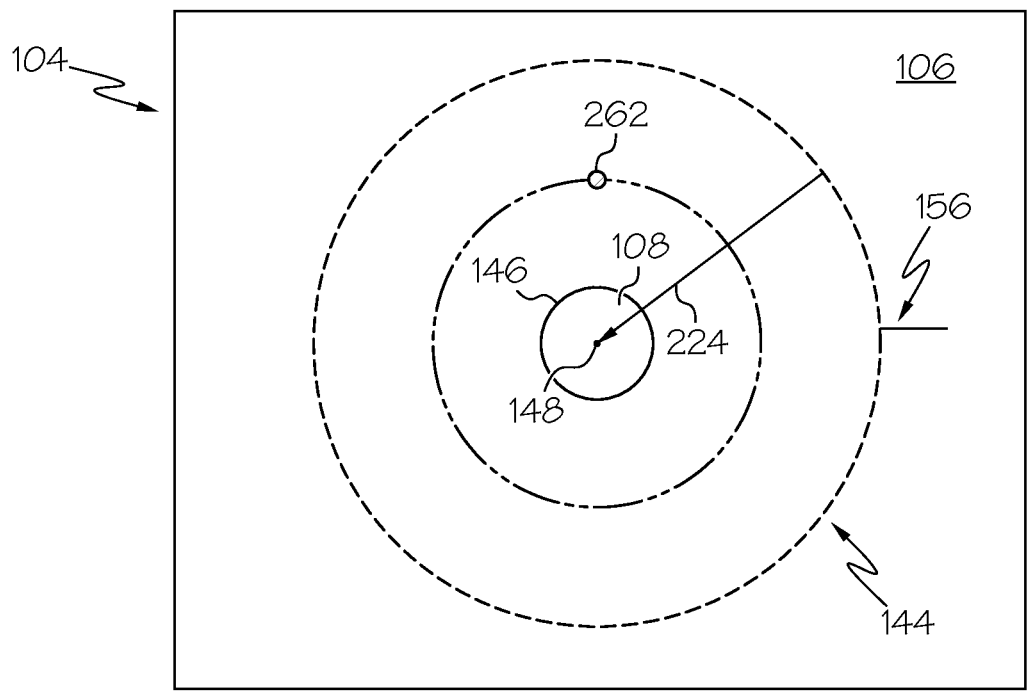
Figure 16:
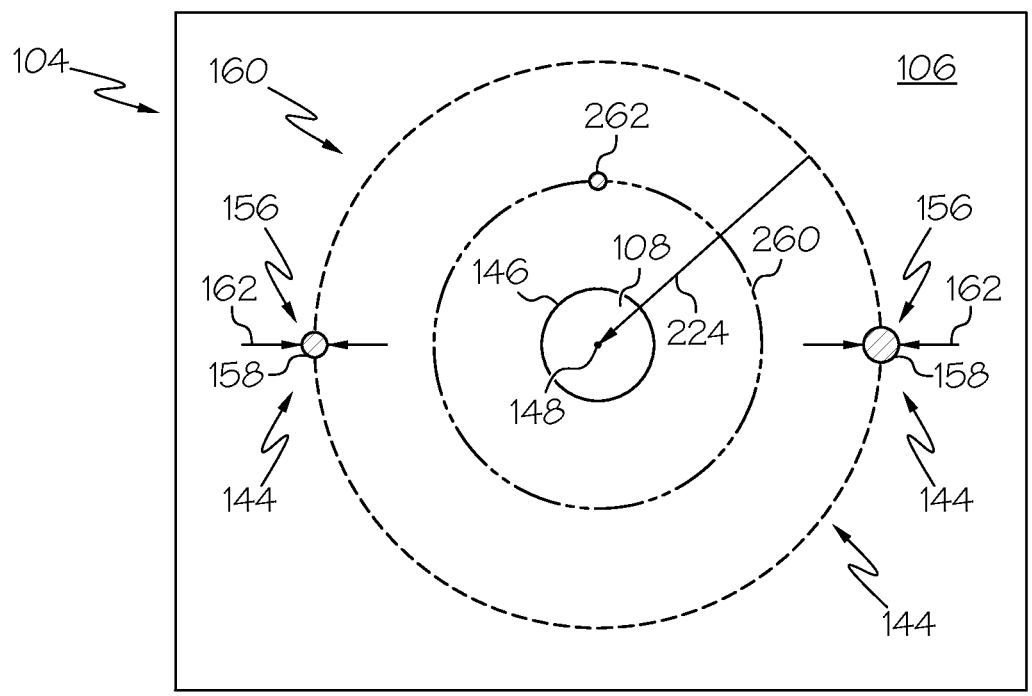
Figure 17:
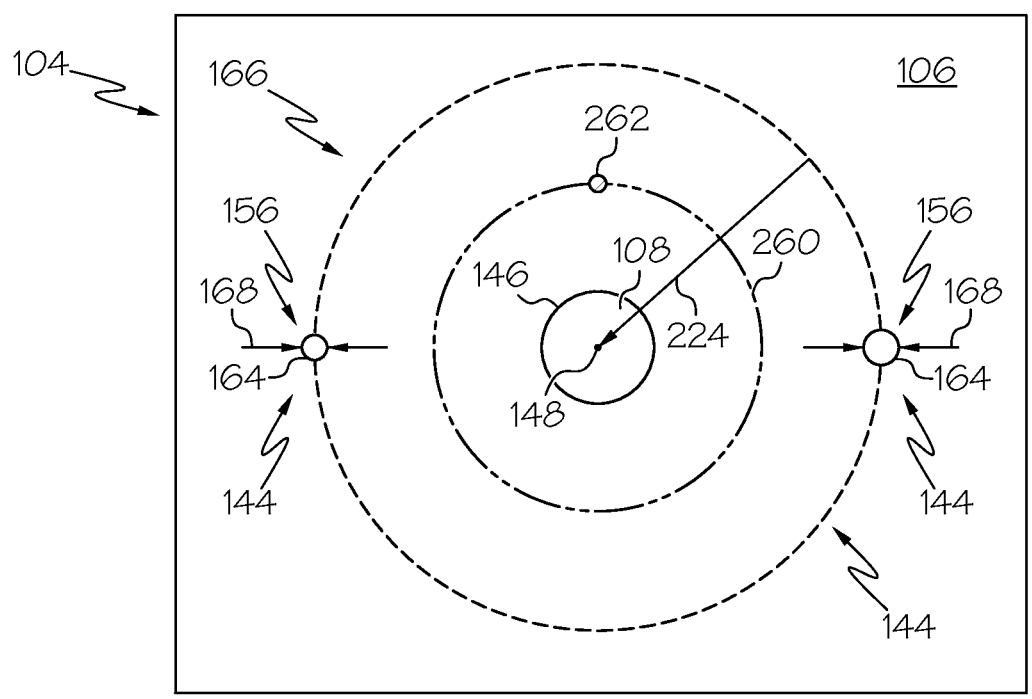
Figure 18:
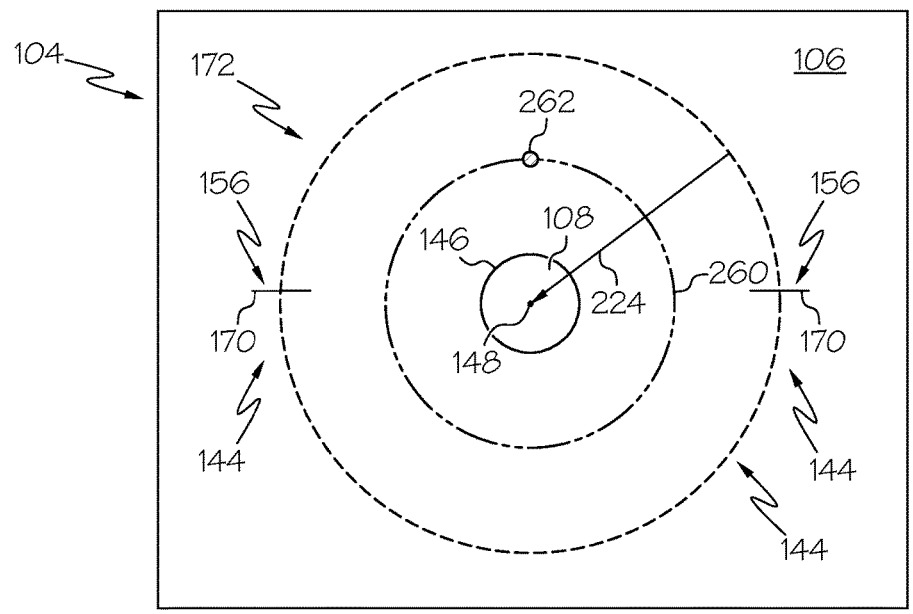
Figure 19:
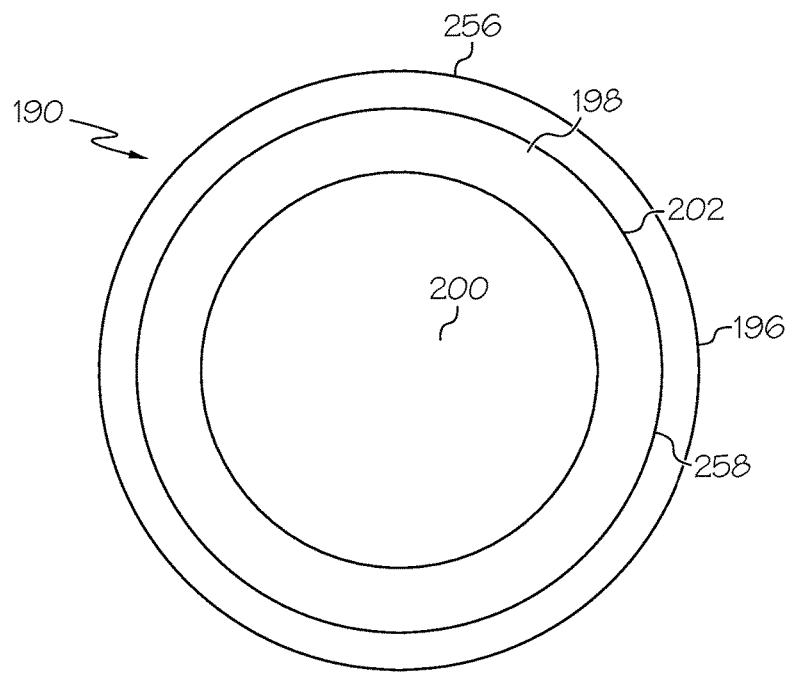
Figure 20:
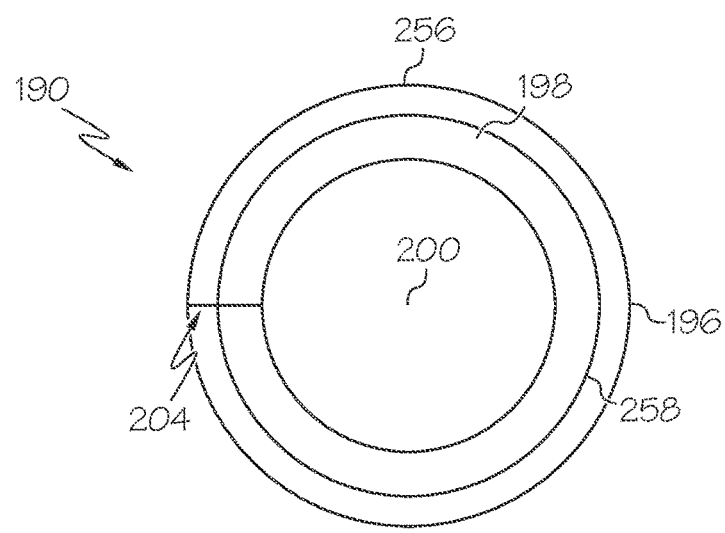
Figure 21:
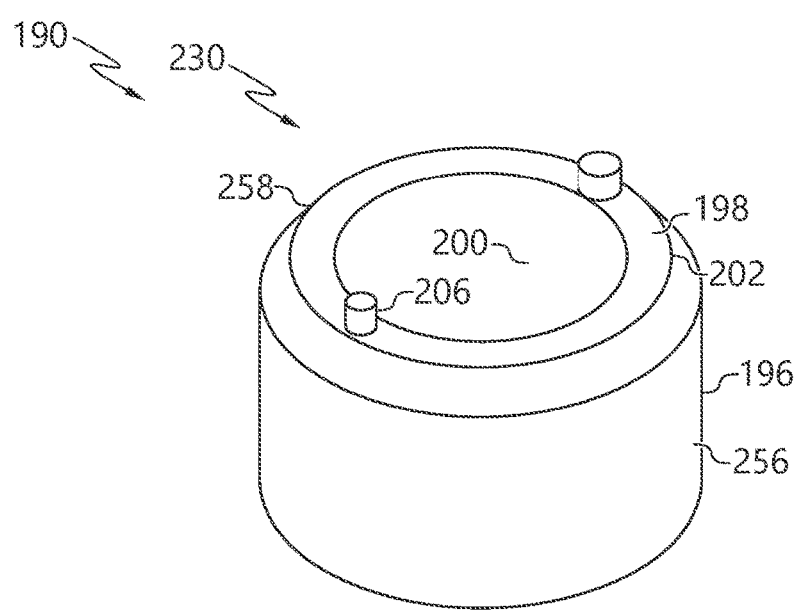
Figure 22:
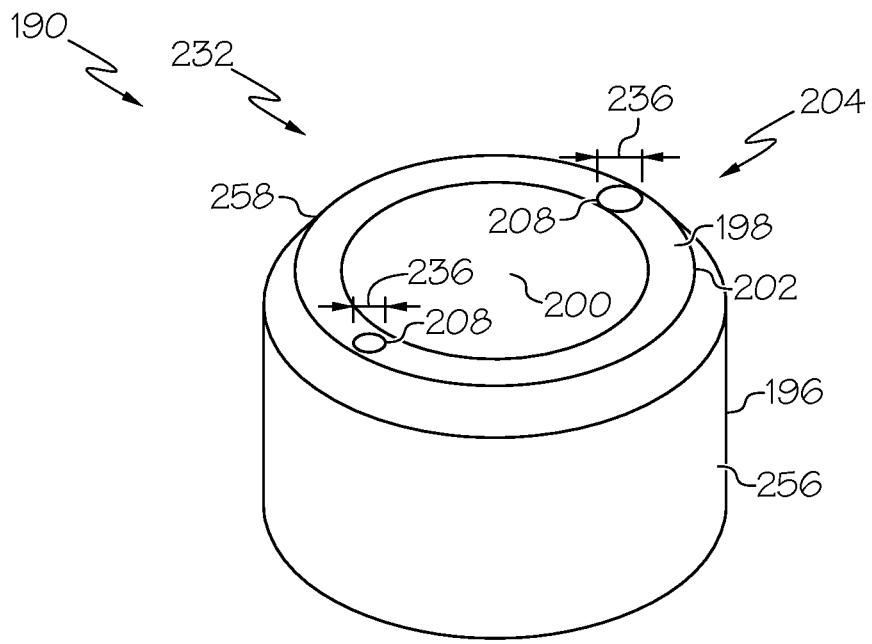
Figure 23:
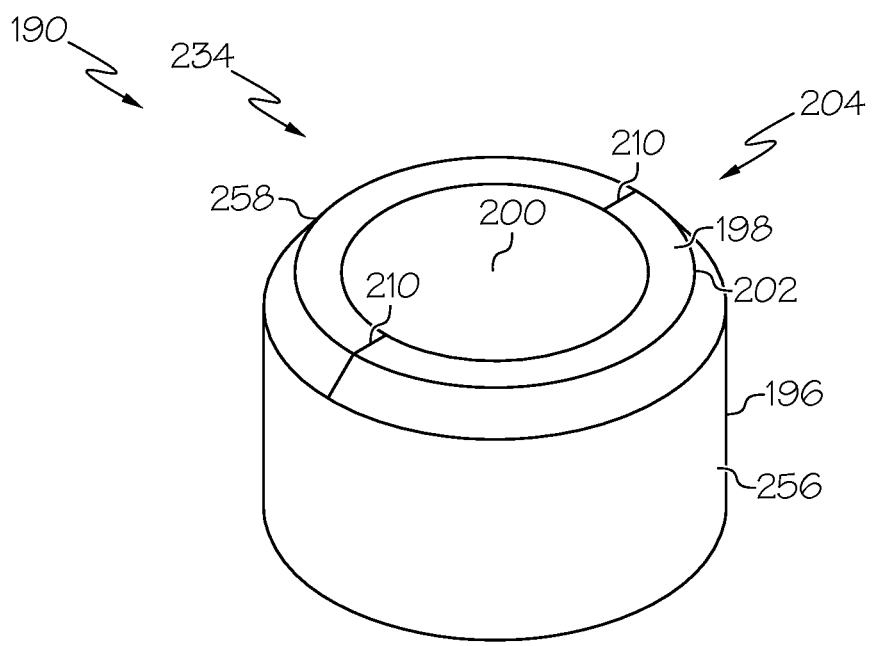
Figure 24:
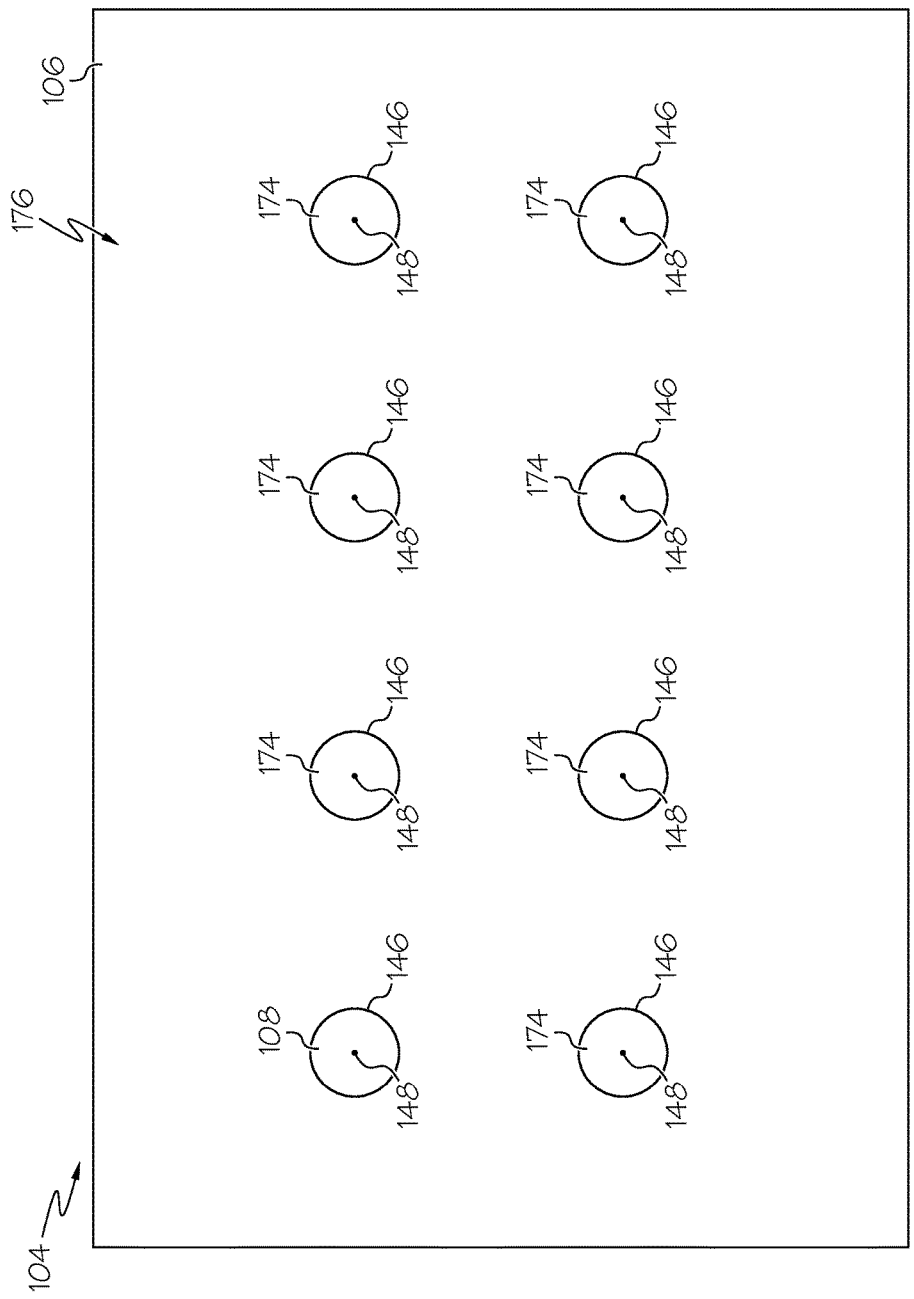
Figure 25:
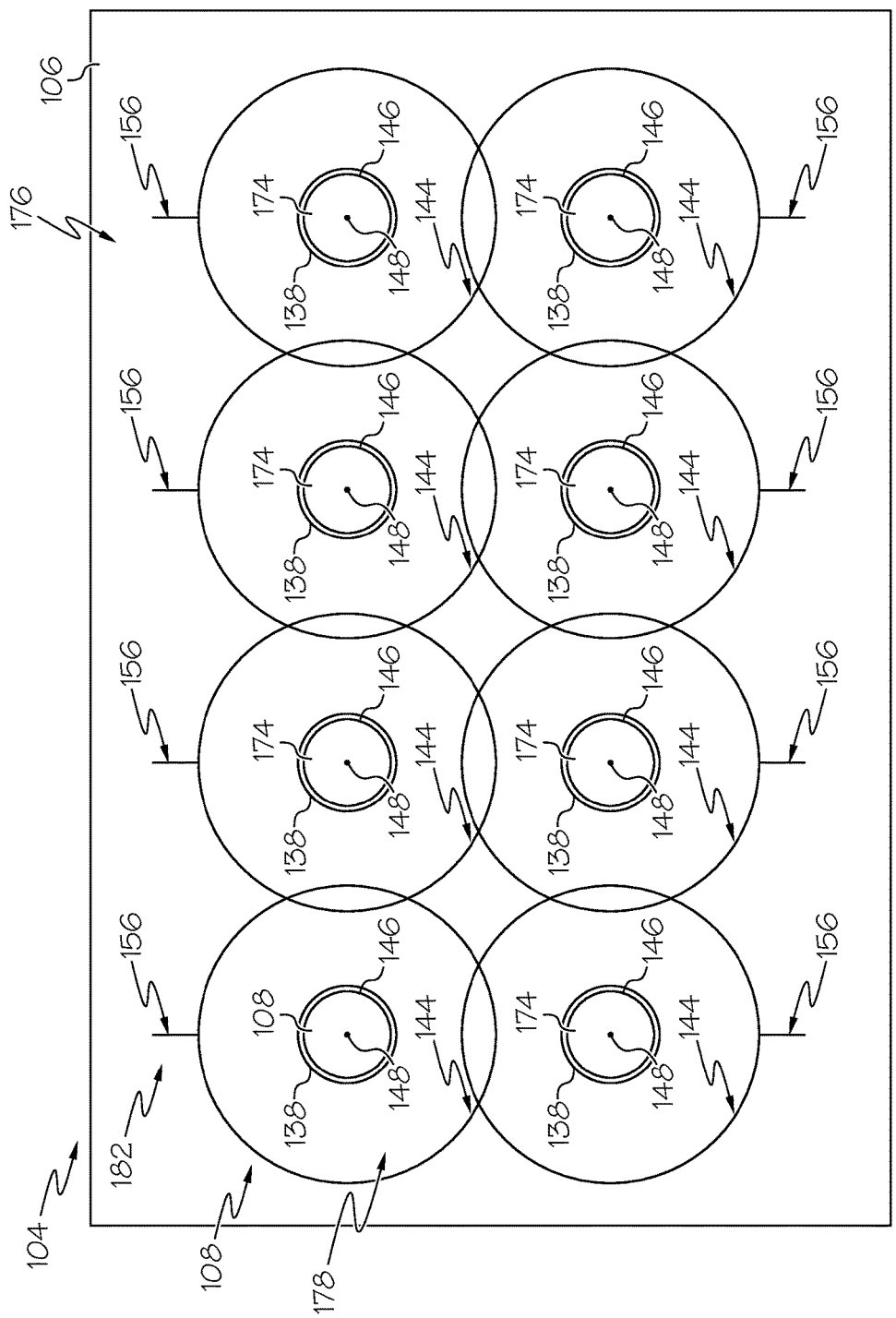
Figure 26A:
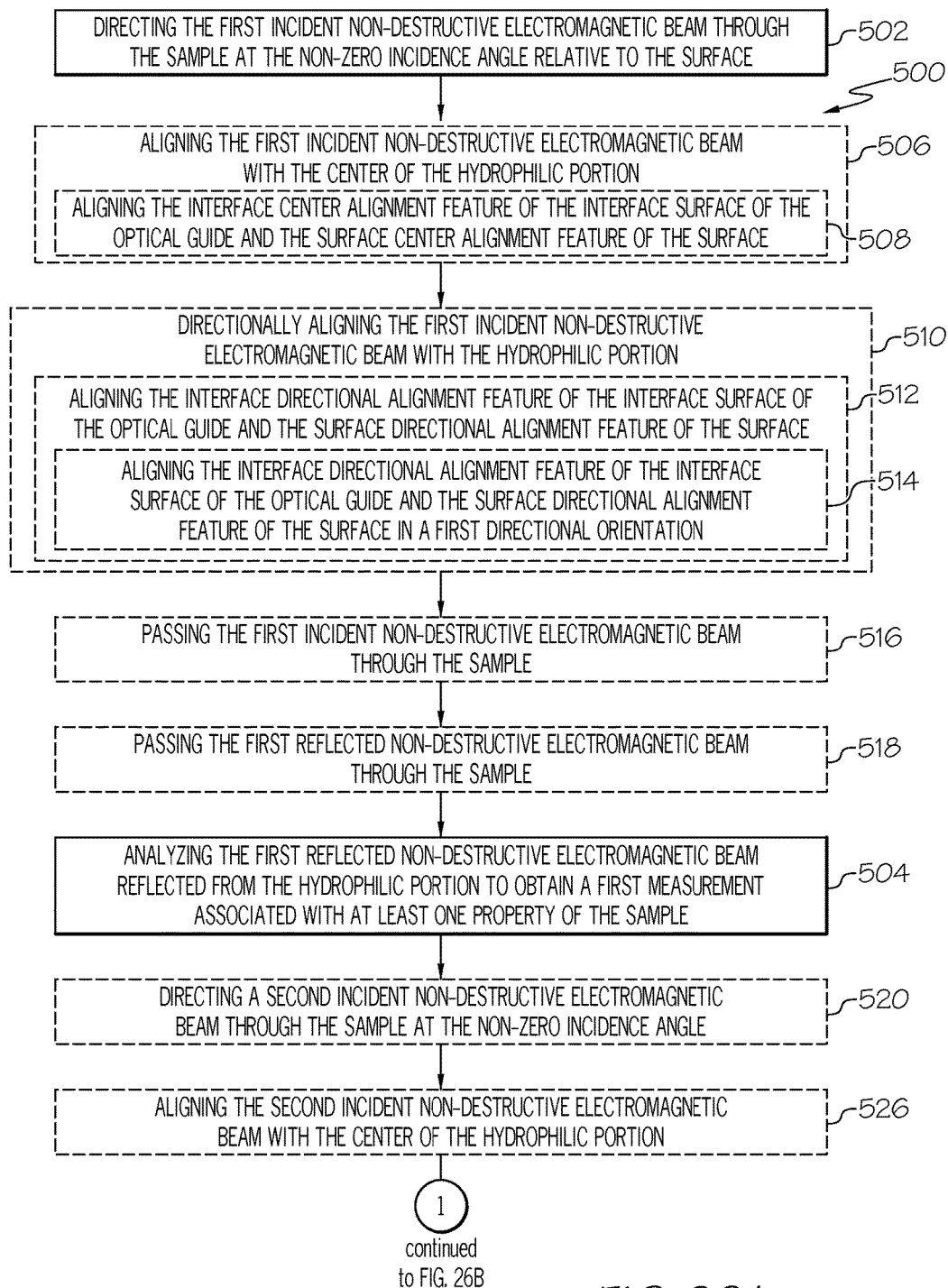
Figure 26B:
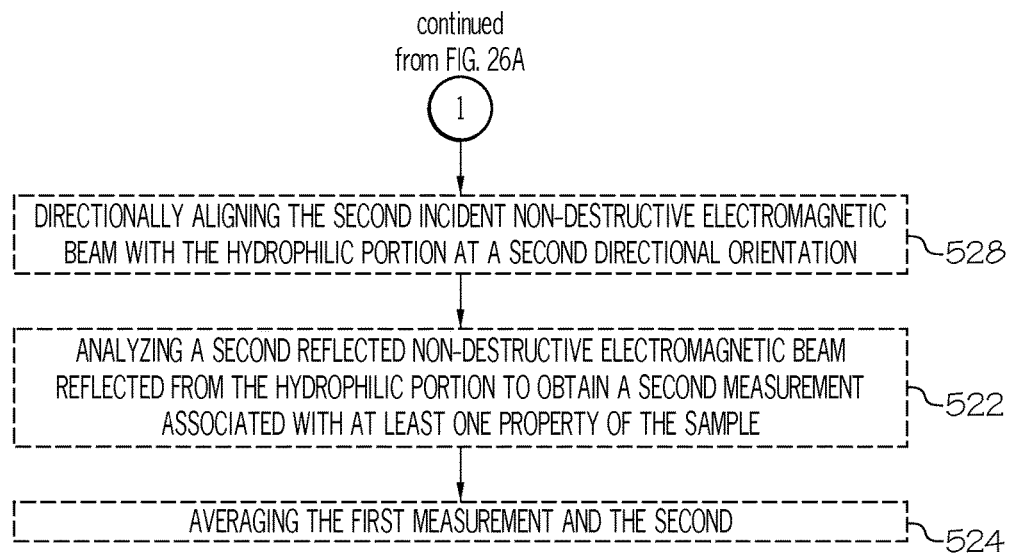
Figure 27:
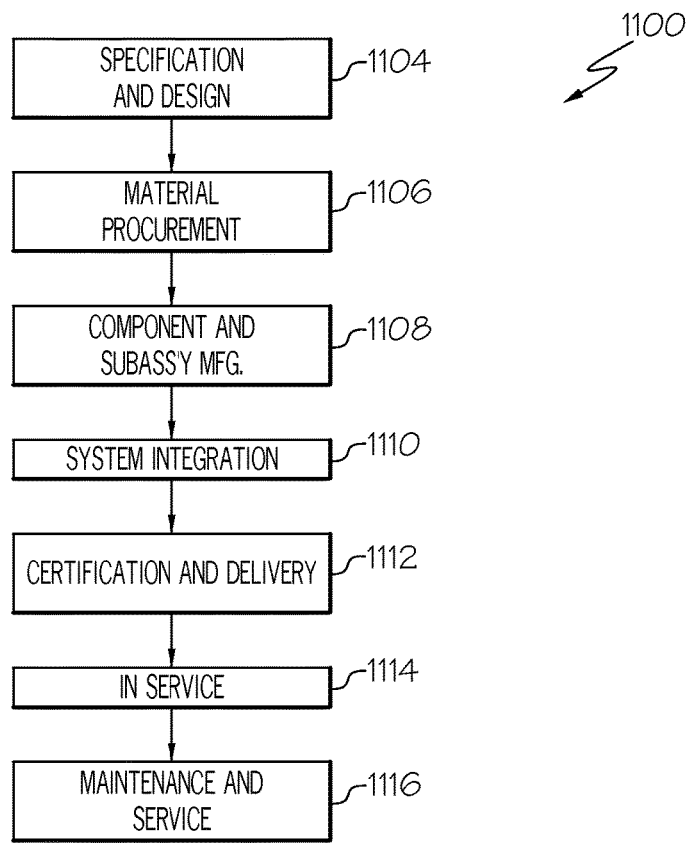

Having thus described examples of the disclosure in general terms, reference will now be made to the accompanying drawings, which are not necessarily drawn to scale, and wherein like reference characters designate the same or similar parts throughout the several views, and wherein:

FIGS. 1A and 1B are a block diagram of an apparatus for spectroscopic analysis of residue, according to one aspect of the present disclosure;

FIG. 2 is a schematic perspective view of a hydrophobic portion and a hydrophilic portion represented in FIGS. 1A and 1B, according to one aspect of the disclosure;

FIG. 3 is a schematic plan view of the hydrophobic portion and the hydrophilic portion of FIG. 2, according to one aspect of the disclosure;

FIG. 4 is a schematic sectional view of the hydrophobic portion and the hydrophilic portion of FIG. 3, according to one aspect of the disclosure;

FIG. 5 is a schematic sectional view of the hydrophobic portion and the hydrophilic portion of FIG. 3, according to one aspect of the disclosure;

FIG. 6 is a schematic plan view of an identifying feature associated with a hydrophilic portion represented in FIGS. 1A and 1B, according to one aspect of the disclosure;

FIG. 6A is a schematic plan view of an identifying feature associated with a hydrophilic portion represented in FIGS. 1A and 1B, according to one aspect of the disclosure;

FIG. 7 is a schematic plan view of an identifying feature associated with a hydrophilic portion represented in FIGS. 1A and 1B, according to one aspect of the disclosure;

FIG. 8 is a schematic view of means for generating a first incident non-destructive electromagnetic beam, means for detecting a first reflected non-destructive electromagnetic beam, and an optical guide of the apparatus of FIGS. 1A and 1B, according to one aspect of the disclosure;

FIG. 9 is a schematic view of the first incident non-destructive electromagnetic beam and the first reflected non-destructive electromagnetic beam represented in FIG. 8, according to one aspect of the disclosure;

FIG. 10 is a schematic plan view of a surface center alignment feature associated with a hydrophilic portion of a surface of the apparatus of FIGS. 1A and 1B, according to one aspect of the disclosure;

FIG. 11 is a schematic plan view of a surface centering projection of the surface center alignment feature represented in FIG. 10, according to one aspect of the disclosure;

FIG. 12 is a schematic plan view of a surface centering depression of the surface center alignment feature represented in FIG. 10, according to one aspect of the disclosure;

FIG. 13 is a schematic plan view of a surface centering marking of the surface center alignment feature represented in FIG. 10, according to one aspect of the disclosure;

FIG. 14 is a schematic plan view of a surface directional alignment feature associated with a hydrophilic portion of a surface of the apparatus of FIGS. 1A and 1B, according to one aspect of the disclosure;

FIG. 15 is a schematic plan view of a surface directional alignment feature associated with a hydrophilic portion of a surface of the apparatus of FIGS. 1A and 1B, according to one aspect of the disclosure;

FIG. 16 is a schematic plan view of a surface directing projection of the surface directional alignment feature represented in FIGS. 14 and 15, according to one aspect of the disclosure;

FIG. 17 is a schematic plan view of a surface directing depression of the surface directional alignment feature represented in FIGS. 14 and 15, according to one aspect of the disclosure;

FIG. 18 is a schematic plan view of a surface directing color marking of the surface directional alignment feature represented in FIGS. 14 and 15, according to one aspect of the disclosure;

FIG. 19 is a schematic plan view of an interface center alignment feature of an interface surface of an optical guide of the apparatus of FIGS. 1A and 1B, according to one aspect of the disclosure;

FIG. 20 is a schematic plan view of an interface directional alignment feature of an interface surface of an optical guide of the apparatus of FIGS. 1A and 1B, according to one aspect of the disclosure;

FIG. 21 is a schematic side perspective view of an interface directing projection of an interface surface of an optical guide of the apparatus of FIGS. 1A and 1B, according to one aspect of the disclosure;

FIG. 22 is a schematic side perspective view of an interface directing depression of an interface surface of an optical guide of the apparatus of FIGS. 1A and 1B, according to one aspect of the disclosure;

FIG. 23 is a schematic side perspective view of an interface directing color marking of an interface surface of an optical guide of the apparatus of FIGS. 1A and 1B, according to one aspect of the disclosure;

FIG. 24 is a schematic plan view of a plurality of hydrophilic portions of a surface of the apparatus of FIGS. 1A and 1B, according to one aspect of the disclosure;

FIG. 25 is a schematic plan view of a plurality of a plurality of identifying features, a plurality of surface center alignment features, and a plurality of surface directional alignment features associated with the hydrophilic portions represented in FIG. 24, according to one aspect of the disclosure;

FIGS. 26A and 26B are a block diagram of a method for analyzing a sample located on the hydrophilic portion of the surface of the apparatus, according to one aspect of the disclosure;

FIG. 27 is a block diagram of aircraft production and service methodology; and

Figure 28:
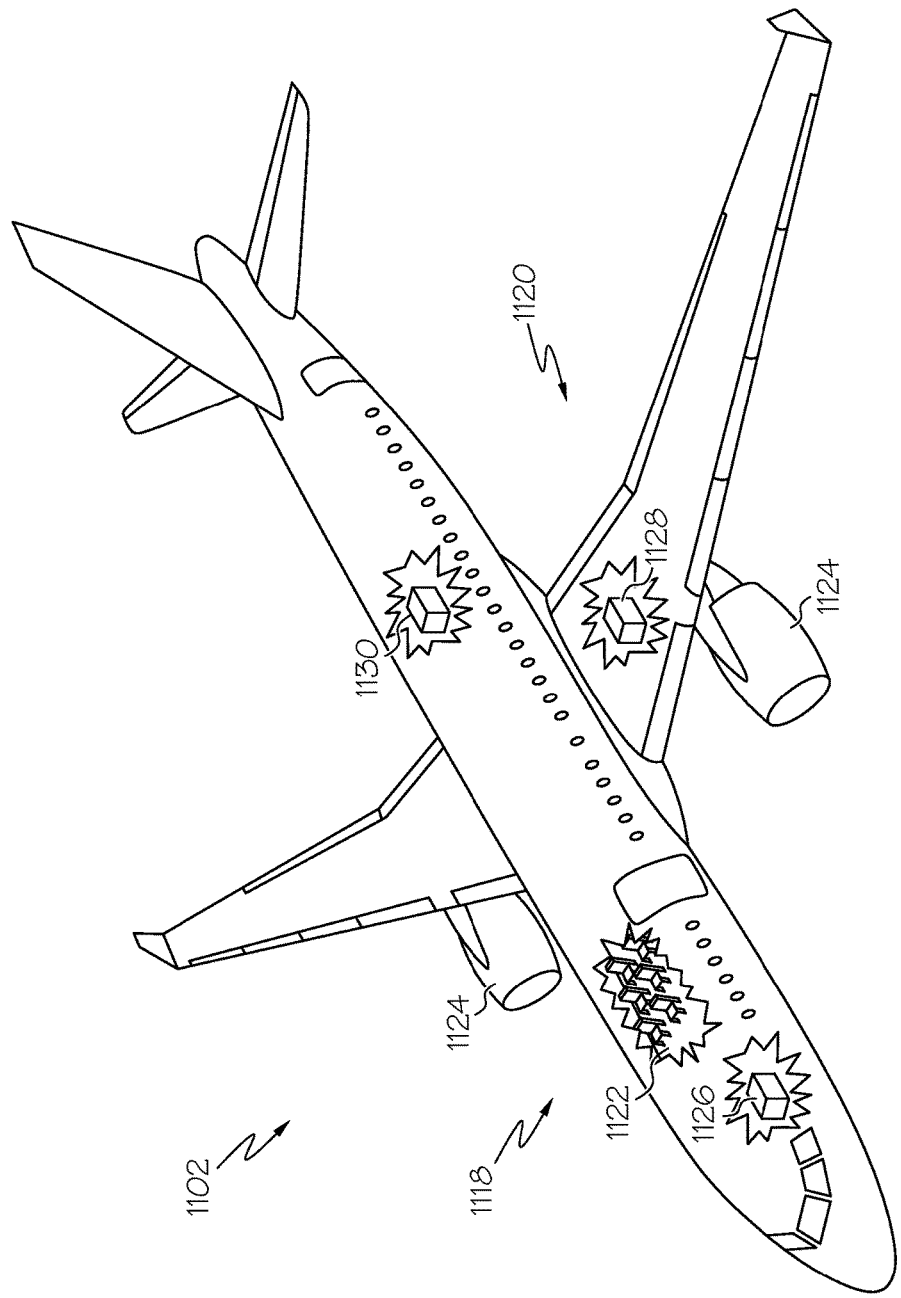

FIG. 28 is a schematic illustration of an aircraft.

In the block diagram(s) referred to above, solid lines, if any, connecting various elements and/or components may represent mechanical, electrical, fluid, optical, electromagnetic and other couplings and/or combinations thereof. As used herein, "coupled" means associated directly as well as indirectly. For example, a member A may be directly associated with a member B, or may be indirectly associated therewith, e.g., via another member C. Couplings other than those depicted in the block diagrams may also exist. Dashed lines, if any, connecting the various elements and/or components represent couplings similar in function and purpose to those represented by solid lines; however, couplings represented by the dashed lines may either be selectively provided or may relate to alternative or optional aspects of the disclosure. Likewise, elements and/or components, if any, represented with dashed lines, indicate alternative or optional aspects of the disclosure. Environmental elements, if any, are represented with dotted lines.

In the block diagram(s) referred to above, the blocks may also represent operations and/or portions thereof. Lines connecting the various blocks do not imply any particular order or dependency of the operations or portions thereof.

DETAILED DESCRIPTION

In the following description, numerous specific details are set forth to provide a thorough understanding of the disclosed concepts, which may be practiced without some or all of these particulars. In other instances, details of known devices and/or processes have been omitted to avoid unnecessarily obscuring the disclosure. While some concepts will be described in conjunction with specific examples, it will be understood that these examples are not intended to be limiting.

Reference herein to "one example" or "one aspect" means that one or more feature, structure, or characteristic described in connection with the example or aspect is included in at least one implementation. The phrase "one example" or "one aspect" in various places in the specification may or may not be referring to the same example or aspect.

Referring generally to FIGS. 1A, 1B and 2-14, and with particular reference to FIGS. 1A, 1B, 2 and 3, one example of the present disclosure relates to an apparatus 100 for spectroscopic analysis of residue 102. The apparatus 100 includes a surface 104, including a hydrophobic portion 106 and a hydrophilic portion 108. The hydrophobic portion 106 surrounds the hydrophilic portion 108. The hydrophilic portion 108 includes a dimension 110 equal to or larger than a width 112 of a first incident non-destructive electromagnetic beam 114.

As used herein, spectroscopic analysis may include the measurement of an interaction between radiative energy (e.g., the first non-destructive electromagnetic beam 114) and specific types of matter (e.g., residue 102), for example, the measurement of radiation intensity of electromagnetic radiation as a function of wavelength. The term non-destructive electromagnetic beam may include any focused electromagnetic radiation that does not damage or destroy the matter interacted with by the electromagnetic radiation.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

In one example implementation of the disclosed apparatus 100, a sample 212 may be deposited on the hydrophilic portion 108 for spectroscopic analysis of the residue 102. The sample 212 may also be referred to as an analyte that is of interest in a spectroscopic analysis procedure, such as a method 500 for analyzing the sample 212 located on the hydrophilic portion 108 of the surface 104 as described herein below (e.g., FIG. 15). As one example, the sample 212 may include a liquid solvent and the residue 102. As one example, the liquid solvent may be water. As one example, the liquid solvent may be an organic solvent including, but not limited to, acetonitrile, dimethylformamide, dimethylsulfoxide, methanol, ethanol, acetone, methylene chloride, methyl ethyl ketone, hexane, toluene, tetrahydrofuran and dichloromethane. As one example, the liquid solvent may be water and the organic solvent.

Referring, e.g., to FIG. 2, as used herein, the width 112 of the first incident non-destructive electromagnetic beam 114 may be defined as a cross-sectional dimension (e.g., a linear distance perpendicular to a centerline 239 of the first incident non-destructive electromagnetic beam 114 and between two opposed points disposed at an exterior boundary) of the first incident non-destructive electromagnetic beam 114 proximate (e.g., at or near) the hydrophilic portion 108. As one example, the width 112 of the first incident non-destructive electromagnetic beam 114 may be defined at a point of impact with the hydrophilic portion 108 and/or the residue 102.

The first non-destructive electromagnetic beam 114 (e.g., electromagnetic radiation) may include various wavelengths. As one example, the first non-destructive electromagnetic beam 114 may include infrared light. As one example, the first non-destructive electromagnetic beam 114 may include ultraviolet light.

Referring, e.g., to FIG. 3, in example, the hydrophilic portion 108 includes a peripheral boundary 146 and a center 148 circumscribed by the peripheral boundary 146.

The peripheral boundary 146 of the hydrophilic portion 108 may define any shape 242. As one example, the shape 242 defined by the peripheral boundary 146 of the hydrophilic portion 108 may be circular. As one example, the shape 242 defined by the peripheral boundary 146 of the hydrophilic portion 108 may be ovular. As one example, the shape 242 defined by the peripheral boundary 146 of the hydrophilic portion 108 may be elliptical. As one example, the shape 242 defined by the peripheral boundary 146 of the hydrophilic portion 108 may be polygonal.

The dimension 110 of the hydrophilic portion 108 may be defined as a linear distance between two opposed points on the peripheral boundary 146 of the hydrophilic portion 108. As one general, non-limiting example, the dimension 110 of the hydrophilic portion 108 may be defined as the smallest linear distance between two opposed points on the peripheral boundary 146 of the hydrophilic portion 108. As one specific, non-limiting example, the dimension 110 may be a diameter for a circular-shaped hydrophilic portion 108. As one specific, non-limiting example, the dimension 110 may be a minor diameter for an ovular-shaped or elliptical shaped hydrophilic portion 108.

Referring, e.g., to FIG. 3, in one aspect of the disclosure, which may include at least a portion of the subject matter of any of the preceding and/or following examples and aspects, the dimension 110 of the hydrophilic portion 108 is at least 5 mm.

Referring, e.g., to FIG. 3, in one aspect of the disclosure, which may include at least a portion of the subject matter of any of the preceding and/or following examples and aspects, the dimension 110 of the hydrophilic portion 108 is at least 7 mm.

Referring, e.g., to FIGS. 2 and 3, in one aspect of the disclosure, which may include at least a portion of the subject matter of any of the preceding and/or following examples and aspects, the hydrophilic portion 108 is optically reflective. As used herein, optically reflective may include reflection characteristics that yield a reflectivity of between 80 percent and 100 percent of the first incident non-destructive electromagnetic beam 114 (e.g., FIG. 2).

Referring, e.g., to FIG. 2, in one aspect of the disclosure, which may include at least a portion of the subject matter of any of the preceding and/or following examples and aspects, the surface 104 is formed on a plate 116. As one example, the surface 104 may include a flat, optically smooth surface formed on the plate 116.

Referring, e.g., to FIGS. 1A and 1B, in one aspect of the disclosure, which may include at least a portion of the subject matter of any of the preceding and/or following examples and aspects, the plate 116 includes a metallic body 118. As one example, the metallic body 118 may be stainless steel. As one example, the metallic body 118 may be aluminum.

Referring, e.g., to FIG. 1, in one aspect of the disclosure, which may include at least a portion of the subject matter of any of the preceding and/or following examples and aspects, the plate 116 includes a plastic body 120 and a metal coating 122 at least partially covering the plastic body 120. As one example, the plastic body 120 may be formed from any suitable thermoset and/or thermoplastic materials. As one example, the metal coating 122 may be aluminum. As one example, the metal coating 122 may be nickel. As one example, the metal coating 122 may be chrome.

Referring, e.g., to FIG. 4, in one aspect of the disclosure, which may include at least a portion of the subject matter of any of the preceding and/or following examples and aspects, the hydrophobic portion 106 includes a substantially uniform coating 124 of a hydrophobic material 126. As one example, the hydrophobic portion 106 includes a substantially continuous coating 124 of a hydrophobic material 126. As one example, the coating 124 of a hydrophobic material 126 may be applied to (e.g., cover) at least a portion of a surface of the plate 116. As one example, the hydrophobic material may include, but is not limited to, long chain alkane hydrocarbons, such as, C8, C12, and C18.

As one example, the uniform coating 124 of the hydrophobic material 126 is optically reflective. As one example, the uniform coating 124 of the hydrophilic material 126 is transparent and the plate 116 (e.g., the surface of the plate 116) is optically reflective.

Referring, e.g., to FIG. 4, in one aspect of the disclosure, which may include at least a portion of the subject matter of any of the preceding and/or following examples and aspects, the hydrophilic portion 108 includes a substantially uniform coating 128 of a hydrophilic material 130. As one example, the coating 128 of the hydrophilic material 130 may be applied to (e.g., cover) at least a portion of a surface of the coating 124 of a hydrophobic material 126. As one example, the hydrophilic material 130 may include, but is not limited to, materials including molecules with polar functional groups, such as, cyano groups or carboxyl groups, or multiple hydroxyl groups, such as polysaccharide or glycol.

Referring, e.g., to FIG. 5, in one aspect of the disclosure, which may include at least a portion of the subject matter of any of the preceding and/or following examples and aspects, the hydrophobic portion 106 includes a hydrophobic substrate 132. The hydrophilic portion 108 is defined by an absence of the hydrophobic substrate 132. As one example, the hydrophobic substrate 132 may be formed from the hydrophobic material 126. The hydrophobic substrate 132 may be locally removed to expose the hydrophilic portion 108 by any suitable machining, etching and/or chemical process.

Referring, e.g., to FIG. 5, in one aspect of the disclosure, which may include at least a portion of the subject matter of any of the preceding and/or following examples and aspects, the hydrophobic substrate 132 is connected to the plate 116. The hydrophobic substrate 132 may be connected to the plate 116 by any suitable operation and/or process. As one example, the hydrophobic substrate 132 may be chemically bonded to the plate 116 (e.g., to the surface of the plate 116). As one example, the hydrophobic substrate 132 may be adhered to the plate 116 (e.g., to the surface of the plate 116).

In one example construction, the plate 116 may include a thickness 238. As one example, the thickness 238 of the plate 116 may be up to 0.3 mm. As one example, the thickness 238 of the plate 116 may be up to 0.5 mm. As one example, the thickness 238 of the plate 116 may be up to 1 mm. As one example, the thickness 238 of the plate 116 may be greater than 1 mm.

In one example construction, the hydrophobic substrate 132 may include a thickness 240. As one example, the thickness 240 of the hydrophobic substrate 132 may be up to 10 nm. As one example, the thickness 240 of the hydrophobic substrate 132 may be up to 25 nm. As one example, the thickness 240 of the hydrophobic substrate 132 may be up to 50 nm. As one example, the thickness 240 of the hydrophobic substrate 132 may be greater than 50 nm. Those skilled in the art will recognize that the thickness 240 may depend on the optical properties of the hydrophilic substrate 132 and/or the wavelength of the first non-destructive electromagnetic beam 114.

Referring, e.g., to FIG. 5, in one aspect of the disclosure, which may include at least a portion of the subject matter of any of the preceding and/or following examples and aspects, the hydrophilic portion 108 includes a portion 136 of the plate 116 characterized by an absence of the hydrophobic substrate 132. As one example, the hydrophilic portion 108 includes a portion of the surface 104 characterized by an absence of the hydrophobic substrate 132. As one example, the absence of the hydrophobic substrate 132 may be defined by removing at least a portion of the hydrophobic substrate 132 from the plate 116 to expose the portion 136 of the plate 116. The hydrophilic portion 108 may be defined by the portion 136 of the plate 116 not having the hydrophobic substrate 132 connected and/or applied to it.

Referring, e.g., to FIG. 5, in one aspect of the disclosure, which may include at least a portion of the subject matter of any of the preceding and/or following examples and aspects, at least the portion 136 of the plate 116, characterized by the absence of the hydrophobic substrate 132, is optically reflective.

Referring, e.g., to FIGS. 6 and 7, in one aspect of the disclosure, which may include at least a portion of the subject matter of any of the preceding and/or following examples and aspects, the surface 104 includes an identifying feature 138 associated with the hydrophilic portion 108. The identifying feature 138 may distinguish (e.g., visually distinguish) the hydrophilic portion 108 from the hydrophobic portion 106. In such a manner, the peripheral boundary 146 and/or the center 148 of the hydrophilic portion 108 may be significantly easier to locate on the surface 104. As a result, the residue 102 (e.g., the sample 212) may be deposited on the hydrophilic portion 108 consistently. As one example, the residue 102 may be deposited proximate (e.g., at or near) the center 148 of the hydrophilic portion 108. As one example, the residue 102 may be evenly applied to the hydrophilic portion 108 within the peripheral boundary 146. As such, the time required to locate the hydrophilic portion 108 and to deposit the residue 102 on the hydrophilic portion 108 may be significantly reduced and the accuracy of depositing the residue 102 on the hydrophilic portion 108 may be significantly increased.

As one example, the identifying feature 138 may be etched into the surface 104. As one example, the identifying feature 138 may be machined into the surface 104. As one example, the identifying feature 138 may be printed onto the surface 104.

As one example, the identifying feature 138 may be at least partially coextensive with the peripheral boundary 146 of the hydrophilic portion 108. In such an example, the peripheral boundary 146 of the hydrophilic portion 108 may define the identifying feature 138.

As one example, the identifying feature 138 may be spaced outward from the peripheral boundary 146 of the hydrophilic portion 108 relative to the center 148. In such an example, the identifying feature 138 may be near to, but not coextensive with, the peripheral boundary 146 of the hydrophilic portion 108.

Referring, e.g., to FIG. 6, in one aspect of the disclosure, which may include at least a portion of the subject matter of any of the preceding and/or following examples and aspects, the identifying feature 138 is a visually identifiable boundary 140 between the hydrophilic portion 108 and the hydrophobic portion 106. As one example, the hydrophobic portion 106 may have a first visual characteristic and the hydrophilic portion 108 may have a second visual characteristic, whereby the visually identifiable boundary 140 corresponds to the peripheral boundary 146 of the hydrophilic portion 108. The first visual characteristic and the second visual characteristic may be different. As one example, the first and second visual characteristics may be color (e.g., the hydrophobic portion 106 may have a first color and the hydrophilic portion 108 may have a second color, wherein the first and second colors are different). As one example, the first and second visual characteristics may be glossiness (e.g., the hydrophobic portion 106 may be glossy and the hydrophilic portion 108 may flat or vice versa).

Referring, e.g., to FIGS. 6A and 7, in one aspect of the disclosure, which may include at least a portion of the subject matter of any of the preceding and/or following examples and aspects, the visually identifiable boundary 140 includes an identifying color marking 142. As one example, the identifying color marking 142 may include a shape 244. The shape 244 of the identifying color marking 142 may substantially match the shape 242 defined by the peripheral boundary 146 of the hydrophilic portion 108. As one example, the identifying color marking 142 may have a color that contrasts a color of the hydrophilic portion 108 and/or a color of the hydrophobic portion 106.

Referring, e.g., to FIG. 6A, in one aspect of the disclosure, which may include at least a portion of the subject matter of any of the preceding and/or following examples and aspects, the identifying color marking 142 is continuous. As one example, the identifying color marking 142 may be a continuous line completely surrounding the peripheral boundary 146 of the hydrophilic portion 108.

Referring, e.g., to FIG. 7, in one aspect of the disclosure, which may include at least a portion of the subject matter of any of the preceding and/or following examples and aspects, the identifying color marking 142 is discontinuous. As one example, the identifying color marking 142 may be a plurality of line segments at least partially surrounding the peripheral boundary 146 of the hydrophilic portion 108. As one example, the identifying color marking 142 may be a plurality of marks at least partially surrounding the peripheral boundary 146 of the hydrophilic portion 108.

Referring, e.g., to FIG. 8, in one aspect of the disclosure, which may include at least a portion of the subject matter of any of the preceding and/or following examples and aspects, the apparatus 100 includes means 184 for generating the first incident non-destructive electromagnetic beam 114, means 186 for detecting a first reflected non-destructive electromagnetic beam 188, and an optical guide 190 selectively optically coupled with the means 184 and the means 186. The optical guide 190 is selectively positioned in contact with the surface 104 adjacent the hydrophilic portion 108.

As used herein, means-plus-function clauses are to be interpreted under 35 U.S.C. 112(f), unless otherwise explicitly stated. It should be noted that examples provided herein of any structure, material, or act in support of any of the means-plus-function clauses, and equivalents thereof, may be utilized individually or in combination. Thus, while various structures, materials, or acts may be described in connection with a means-plus-function clause, any combination thereof or of their equivalents is contemplated in support of such means-plus-function clause.

The means 184 for generating the first incident non-destructive electromagnetic beam 114 may be any device or mechanism (e.g., an emitter) configured to generate and transmit the first incident non-destructive electromagnetic beam 114 (e.g., an incident non-destructive electromagnetic beam source). As one example, the means 184 for generating the first incident non-destructive electromagnetic beam 114 may include a hot filament (e.g., a "glow bar") to generate mid-infrared light. As one example, the means 184 for generating the first incident non-destructive electromagnetic beam 114 may include a black-body radiator. As one example, the means 184 for generating the first incident non-destructive electromagnetic beam 114 may include a halogen bulb to generate near-infrared light.

The means 186 for detecting the first reflected non-destructive electromagnetic beam 188 may be any device or mechanism (e.g., a detector) configured to receive and process (e.g., analyze) the first reflected non-destructive electromagnetic beam 188 (e.g., a reflected non-destructive electromagnetic beam detector). As one example, the means 186 for detecting the first reflected non-destructive electromagnetic beam 188 may include an infrared sensitive material, such as, Deuterated Tri-Glycine Sulfate ("DTGS") or cooled mercury cadmium telluride ("MCT"). As one example, the means 186 for detecting the first reflected non-destructive electromagnetic beam 188 may sort the wavelengths in the first reflected non-destructive electromagnetic beam 188 using a grating. As one example, the means 186 for detecting the first reflected non-destructive electromagnetic beam 188 may sort the wavelengths in the first reflected non-destructive electromagnetic beam 188 by Fourier Transform processing of the first reflected non-destructive electromagnetic beam 188 passing through an interferometer.

In one example, the means 184 for generating the first incident non-destructive electromagnetic beam 114 and the means 186 for detecting the first reflected non-destructive electromagnetic beam 188 may be components of and/or incorporated into a single spectroscopic analyzer 246. As one example, the spectroscopic analyzer 246 may be a portable (e.g., handheld or desktop) spectroscopy tester. As one general, non-limiting example, the spectroscopic analyzer 246 (e.g., the means 184 for generating the first incident non-destructive electromagnetic beam 114 and/or the means 186 for detecting the first reflected non-destructive electromagnetic beam 188) may be an interferometer configured to analyze electromagnetic waves (e.g., light) containing features of absorption and/or emission associated with the residue 102. As one general, non-limiting example, the spectroscopic analyzer 246 may be a Fourier transform infrared ("FTIR") spectroscopic analyzer. As one specific, non-limiting example, the spectroscopic analyzer 246 may be an ExoScan FTIR spectrometer available from Agilent Technologies, Inc. of Santa Clara, Calif.

As one example, the optical guide 190 may be detachable head connected to an exterior housing (e.g., a body) of the spectroscopic analyzer 246. As one general, non-limiting example, the optical guide 190 may be a specular reflectance head. As one specific, non-limiting example, the optical guide 190 may be a grazing angle specular reflectance head. The apparatus 100 may include a plurality of interchangeable optical guides 190.

Referring, e.g., to FIG. 8, in one aspect of the disclosure, which may include at least a portion of the subject matter of any of the preceding and/or following examples and aspects, the optical guide 190 includes a housing 196 including an interface surface 198, and a lens 200 (e.g., an optical element) inside the housing 198. As one example, the housing 196 may form the exterior body of the optical guide 190. The interface surface 198 may define an exterior surface of the housing 196 that is placed in contact with the surface 104. As one example, the optical guide 190 is positioned such that the interface surface 198 is in direct contact with the surface 104 with the lens 200 positioned over the hydrophilic portion 108.

Referring, e.g., to FIG. 9, in one aspect of the disclosure, which may include at least a portion of the subject matter of any of the preceding and/or following examples and aspects, the optical guide 190 selectively directs the first incident non-destructive electromagnetic beam 114 at the hydrophilic portion 108 at a non-zero incidence angle 192 and receives the first reflected non-destructive electromagnetic beam 188 at a non-zero reflective angle 194.

As one example, the incidence angle 192 may be a non-zero angle defined between the first incident non-destructive electromagnetic beam 114 and the surface 104. As one example, the first incident non-destructive electromagnetic beam 114 may be disposed at a non-zero incidence grazing angle 250 with respect to a reference plane 248. The reference plane 248 may be perpendicular to the surface 104.

As one example, the reflective angle 194 may be a non-zero angle defined between the first reflected non-destructive electromagnetic beam 188 and the surface 104. As one example, the first reflected non-destructive electromagnetic beam 188 may be disposed at a non-zero reflective grazing angle 252 with respect to the reference plane 248.

The lens 200 may be optically constructed or configured to direct (e.g., reflect) the first incident non-destructive electromagnetic beam 114 at the incidence angle 192 (or the incidence grazing angle 250) and the first reflected non-destructive electromagnetic beam 188 and the reflective angle 194 (or the reflective grazing angle 252).

Referring, e.g., to FIG. 9, in one aspect of the disclosure, which may include at least a portion of the subject matter of any of the preceding and/or following examples and aspects, the incidence angle 192 and the reflective angle 194 are between 5 degrees and 20 degrees. As one example, the incidence angle 192 and the reflective angle 194 may be between 15 degrees and 90 degrees. As one example, the incidence angle 192 and the reflective angle 194 may be equal.

As one example, the incidence grazing angle 250 and the reflective grazing angle 252 may be between 70 degrees and 85 degrees. As one example, the incidence grazing angle 250 and the reflective grazing angle 252 may be between 0 degrees and 85 degrees. As one example, the incidence grazing angle 250 and the reflective grazing angle 252 may be equal.

Referring, e.g., to FIG. 10 in one aspect of the disclosure, which may include at least a portion of the subject matter of any of the preceding and/or following examples and aspects, the surface 104 includes a surface center alignment feature 144. The surface center alignment feature 144 may aid in the alignment of the first incident non-destructive electromagnetic beam 114 (e.g., FIG. 8) with the center 148 of the hydrophilic portion 108. In such a manner, the first incident non-destructive electromagnetic beam 114 may consistently impinge (e.g., interact with) the residue 102 disposed proximate (e.g., at or near) the center 148 of hydrophilic portion 108. As a result, with each spectroscopic analysis of the residue 102, subsequent (e.g., spaced is time) incident non-destructive electromagnetic beams may impinge the residue 102 at substantially the same location with respect to the center 148 of the hydrophilic portion 108.

Referring, e.g., to FIG. 10, in one aspect of the disclosure, which may include at least a portion of the subject matter of any of the preceding and/or following examples and aspects, the hydrophilic portion 108 includes the peripheral boundary 146 and the center 148 circumscribed by the peripheral boundary 146. The surface center alignment feature 144 is concentric with the center 148 of the hydrophilic portion 108 and at least partially surrounds the peripheral boundary 146 of the hydrophilic portion 108.

The surface center alignment feature 144 may define a shape 254. As one example, the shape 254 defined by the surface center alignment feature 144 may substantially match the shape 242 defined by the peripheral boundary 146 of the hydrophilic portion 108.

Referring, e.g., to FIGS. 10 and 19, the housing 196 of the optical guide 190 may define a shape 256 (e.g., FIG. 19). As one example, the shape 254 defined by the surface center alignment feature 144 (e.g., FIG. 10) may substantially match the shape 256 defined by the housing 196 of the optical guide 190 (e.g., FIG. 19). As one example, the shape 256 defined by the housing 196 may define a shape of the peripheral edge 258 of the interface surface 198.

Referring, e.g., to FIG. 10, in one aspect of the disclosure, which may include at least a portion of the subject matter of any of the preceding and/or following examples and aspects, the surface center alignment feature 144 is spaced away from the peripheral boundary 146 of the hydrophilic portion 108. As one example, the surface center alignment feature 144 may be spaced outward from the peripheral boundary 146 of the hydrophilic portion 108 with respect to the center 148 of the hydrophilic portion 108.

Referring, e.g., to FIGS. 10 and 19, as one example, the surface center alignment feature 144 may be spaced away from the peripheral boundary 146 of the hydrophilic portion 108 (e.g., FIG. 10) a sufficient distance to allow the interface surface 198 of the housing 196 of the optical guide 190 (e.g., FIG. 19) to fit within the surface center alignment feature 144.

Referring, e.g., to FIGS. 10 and 19, in one aspect of the disclosure, which may include at least a portion of the subject matter of any of the preceding and/or following examples and aspects, the surface 104 includes the surface center alignment feature 144 (e.g., FIG. 10), and the interface surface 198 (e.g., FIG. 19) of the optical guide 190 includes an interface center alignment feature 202 corresponding to the surface center alignment feature 144. As one example, the interface center alignment feature 202 may be defined by a peripheral edge 258 of the interface surface 198 of the housing 196 of the optical guide 190.

Referring, e.g., to FIGS. 10 and 19, in one aspect of the disclosure, which may include at least a portion of the subject matter of any of the preceding and/or following examples and aspects, the hydrophilic portion 108 includes the peripheral boundary 146 and the center 148 circumscribed by the peripheral boundary 146 (e.g., FIG. 10). The surface center alignment feature 144 is concentric with the center 148 of the hydrophilic portion 108 and at least partially surrounds the peripheral boundary 146 of the hydrophilic portion 108 (e.g., FIG. 10). The interface center alignment feature 202 (e.g., FIG. 19) of the optical guide 190 is alignable with the surface center alignment feature 144. As one example, the peripheral edge 258 (e.g., FIG. 19) of the interface surface 198 of the housing 196 of the optical guide 190 (e.g., the interface center alignment feature 202) is alignable with the surface center alignment feature 144.

Referring, e.g., to FIG. 11, in one aspect of the disclosure, which may include at least a portion of the subject matter of any of the preceding and/or following examples and aspects, the surface center alignment feature 144 includes at least one surface centering projection 150. As one example, a single continuous surface centering projection 150 may completely surround the peripheral boundary 146 of the hydrophilic portion 108. As one example, one or more surface centering projections 150 may at least partially surround the peripheral boundary 146 of the hydrophilic portion 108. As one example, the surface centering projection 150 may form an interference protruding upwardly from the surface 104 including, but not limited to, a ridge, a bump, a post or the like. As one example, the surface centering projection 150 may be machined or connected onto the surface 104.

Referring, e.g., to FIGS. 11 and 19, the surface centering projection 150 may define a center alignment of the first incident non-destructive electromagnetic beam 114 (e.g., FIGS. 8 and 9) with the center 148 of the hydrophilic portion 108 (e.g., FIG. 11). As one example, the surface centering projection 150 may visually indicate the center alignment by a contour change on the surface 104 and the interface center alignment feature 202 (e.g., the peripheral edge 258) may be positioned with respect to the surface centering projection 150 to center align the first incident non-destructive electromagnetic beam 114. As one example, the surface centering projection 150 may physically indicate the center alignment by the contour change on the surface 104 and the interface center alignment feature 202 (e.g., the peripheral edge 258) may be positioned within the surface centering projection 150 and/or between the surface centering projections 150 to center align the first incident non-destructive electromagnetic beam 114.

Referring, e.g., to FIG. 12, in one aspect of the disclosure, which may include at least a portion of the subject matter of any of the preceding and/or following examples and aspects, the surface center alignment feature 144 includes at least one surface centering depression 152. As one example, a single continuous surface centering depression 152 may completely surround the peripheral boundary 146 of the hydrophilic portion 108. As one example, one or more surface centering depressions 152 may at least partially surround the peripheral boundary 146 of the hydrophilic portion 108. As one example, the surface centering depression 152 may be an interference formed within the surface 104, including, but not limited to, a through hole, an aperture, a recess, a dimple or the like. As one example, the surface centering depression 152 may be machined or etched into the surface 104.

Referring, e.g., to FIGS. 12 and 19, the surface centering depression 152 may define the center alignment of the first incident non-destructive electromagnetic beam 114 (e.g., FIGS. 8 and 9) with the center 148 of the hydrophilic portion 108 (e.g., FIG. 12). As one example, the surface centering depression 152 may visually indicate the center alignment by a contour change on the surface 104 and the interface center alignment feature 202 (e.g., the peripheral edge 258) may be positioned with respect to the surface centering projection 152 to center align the first incident non-destructive electromagnetic beam 114. As one example, the surface centering depression 152 may physically indicate center alignment by the contour change on the surface 104. The surface centering depression 152 may form a recess in the surface 104 completely surrounding the peripheral boundary 146 of the hydrophilic portion 108 (e.g., FIG. 12). The interface surface 198 of the housing 196 of the optical guide 190 (e.g., FIG. 19) may be positioned within the surface centering depression 152 (e.g., the recess) to center align the first incident non-destructive electromagnetic beam 114.

Referring, e.g., to FIG. 13, in one aspect of the disclosure, which may include at least a portion of the subject matter of any of the preceding and/or following examples and aspects, the surface center alignment feature 144 includes at least one surface centering color marking 154. As one example, a single continuous surface centering color marking 154 may completely surround the peripheral boundary 146 of the hydrophilic portion 108. As one example, one or more surface centering color markings 154 may at least partially surround the peripheral boundary 146 of the hydrophilic portion 108. As one example, the surface centering color markings 154 may form a visually identifiable mark on the surface 104, including, but not limited to, a continuous elongated line, a discontinuous line (e.g., a plurality of line segments), a short line or the like. As one example, the surface centering color markings 154 may be printed on the surface 104.

Referring, e.g., to FIGS. 13 and 19, the surface centering color marking 154 may define the center alignment of the first incident non-destructive electromagnetic beam 114 (e.g., FIGS. 8 and 9) with the center 148 of the hydrophilic portion 108 (e.g., FIG. 13). As one example, the surface centering color marking 154 may visually indicate the center alignment by a color change on the surface 104 and the interface center alignment feature 202 (e.g., the peripheral edge 258) may be positioned with respect to (e.g., within and/or between) the surface centering color markings 154 to center align the first incident non-destructive electromagnetic beam 114.

Referring, e.g., to FIGS. 14 and 15, in one aspect of the disclosure, which may include at least a portion of the subject matter of any of the preceding and/or following examples and aspects, the surface 104 includes a surface directional alignment feature 156. The surface directional alignment feature 156 may aid in directional alignment of the first incident non-destructive electromagnetic beam 114 (e.g., FIGS. 8 and 9) with respect to the hydrophilic portion 108, for example, with respect to any particular location or point on the peripheral boundary 146 of the hydrophilic portion 108. In such a manner, the first incident non-destructive electromagnetic beam 114 may consistently impinge (e.g., interact with) the residue 102 at a predefined directional orientation. As a result, with each spectroscopic analysis of the residue 102, subsequent (e.g., spaced is time) incident non-destructive electromagnetic beams may impinge the residue 102 at substantially the same directional orientations.

As used herein, directional orientation may be an angular direction of the first incident non-destructive electromagnetic beam 114 with respect the hydrophilic portion 108, for example, the peripheral boundary 146 of the hydrophilic portion 108. As one example, a first directional orientation 224 is directed toward the center 148 of the hydrophilic portion 108 and is defined with respect to a reference point 262 on the reference circle 260. As one example, and as illustrated in FIGS. 14 and 15, the first directional orientation 224 is disposed at an angular direction of approximately 45 degrees with respect to the reference point 262 of the reference circle 260.

Referring, e.g., to FIG. 14, in one aspect of the disclosure, which may include at least a portion of the subject matter of any of the preceding and/or following examples and aspects, the surface directional alignment feature 156 is at least partially coextensive with the surface center alignment feature 144. As one example, one or more of the surface center alignment features 144 (e.g., the surface centering projection 150 or the surface centering depression 152) may function as one or more surface directional alignment features 156.

Referring, e.g., to FIG. 15, in one aspect of the disclosure, which may include at least a portion of the subject matter of any of the preceding and/or following examples and aspects, the hydrophilic portion 108 includes the center 148, and the surface directional alignment feature 156 is outward of the surface center alignment feature 144 relative to the center 148 of the hydrophilic portion 108.

Referring, e.g., to FIGS. 15 and 20, in one aspect of the disclosure, which may include at least a portion of the subject matter of any of the preceding and/or following examples and aspects, the surface 104 includes the surface directional alignment feature 156 (e.g., FIG. 15), and the interface surface 198 (e.g., FIG. 20) of the optical guide 190 includes an interface directional alignment feature 204 corresponding to the surface directional alignment feature 156.

Referring, e.g., to FIG. 16, in one aspect of the disclosure, which may include at least a portion of the subject matter of any of the preceding and/or following examples and aspects, the surface directional alignment feature 156 includes at least one surface directing projection 158.

Referring, e.g., to FIG. 16, in one aspect of the disclosure, which may include at least a portion of the subject matter of any of the preceding and/or following examples and aspects, the surface directional alignment feature 156 includes a plurality 160 of surface directing projections (as an example, two surface directing projections 158 are illustrated). Corresponding dimensions 162 of at least one surface directing projection 158 of the plurality 160 of surface directing projections and at least one other surface directing projection 158 of the plurality of surface directing projections are different. In this example, the surface directing projections 158 having different corresponding dimensions 162 may also serve as the surface center alignment feature 144.

Referring e.g., to FIG. 16, in one aspect of the disclosure, which may include at least a portion of the subject matter of any of the preceding and/or following examples and aspects, the surface directional alignment feature 156 includes the plurality 160 of surface directing projections. Corresponding dimensions 162 of all surface directing projections 158 of the plurality 160 of surface directing projections are different.

As one example, the surface directing projections 158 may be an interference projecting upwardly from the surface 104 including, but not limited to, a ridge, a bump, a post or the like. As one example, the surface directing projection 158 may be machined or connected onto the surface 104. As one example, the dimensions 162 of each surface directing projection 158 may be defined as a cross-sectional dimension of the surface directing projection 158.

Referring, e.g., to FIG. 17, in one aspect of the disclosure, which may include at least a portion of the subject matter of any of the preceding and/or following examples and aspects, the surface directional alignment feature 156 includes at least one surface directing depression 164.

Referring, e.g., to FIG. 17, in one aspect of the disclosure, which may include at least a portion of the subject matter of any of the preceding and/or following examples and aspects, the surface directional alignment feature 156 includes a plurality 166 of surface directing depressions (as an example, two surface directing depressions 164 are illustrated). Corresponding dimensions 168 of at least one surface directing depression 164 of the plurality 166 of surface directing depressions and at least one other surface directing depression 164 of the plurality 166 of surface directing depressions are different. In one example, the surface directing depressions 164 having different corresponding dimensions 168 may also serve as the surface center alignment feature 144.

Referring, e.g., to FIG. 17, in one aspect of the disclosure, which may include at least a portion of the subject matter of any of the preceding and/or following examples and aspects, the surface directional alignment feature 156 includes the plurality 166 of surface directing depressions. Corresponding dimensions 168 of all surface directing depressions 164 of the plurality 166 of surface directing depressions are different.

As one example, the surface directing depression 164 may be an interference formed into the surface 104 including, but not limited to, a slot, a through hole, an aperture, a dimple or the like. As one example, the surface directing depression 164 may be machined or etched onto the surface 104. As one example, the dimensions 168 of each surface directing depression 164 may be defined as a cross-sectional dimension of the surface directing depression 164.

Referring, e.g., to FIG. 18, in one aspect of the disclosure, which may include at least a portion of the subject matter of any of the preceding and/or following examples and aspects, the surface directional alignment feature 156 includes at least one surface directing color marking 170.

Referring, e.g., to FIG. 18, in one aspect of the disclosure, which may include at least a portion of the subject matter of any of the preceding and/or following examples and aspects, the surface directional alignment feature 156 includes a plurality 172 of surface directing color markings (as an example, two surface directing color markings 170 are illustrated). At least one surface directing color marking 170 of the plurality 172 of surface directing color markings is different than at least one other surface directing color marking 170 of the plurality 172 of surface directing color markings. In one example, different surface directing color markings 170 may also serve as the surface center alignment feature 144.

Referring, e.g., to FIG. 18, in one aspect of the disclosure, which may include at least a portion of the subject matter of any of the preceding and/or following examples and aspects, the surface directional alignment feature 156 includes the plurality 172 of surface directing color markings. All surface directing color markings 170 of the plurality 172 of surface directing color markings are different.

As one example, the surface directing color marking 170 may form a visually identifiable mark on the surface 104, including, but not limited to, a continuous elongated line, a discontinuous line (e.g., a plurality of line segments), a short line, an alphabetic character, numeric character, a symbol, a shape or the like. As one example, the surface directing color markings 170 may be printed on the surface 104.

Referring, e.g., to FIGS. 16-18 and 21-23, in one aspect of the disclosure, which may include at least a portion of the subject matter of any of the preceding and/or following examples and aspects, the surface directional alignment feature 156 includes at least one of: at least one surface directing projection 158 (e.g., FIG. 16); at least one surface directing depression 164 (e.g., FIG. 17); or at least one surface directing color marking 170 (e.g., FIG. 18). The interface directional alignment feature 204 of the optical guide 190 includes at least one of: at least one interface directing projection 206 (e.g., FIG. 21; as an example, two interface directing projections 206 are illustrated), alignable with the at least one surface directing depression 164; at least one interface directing depression 208 (e.g., FIG. 22; as an example, two interface directing depressions 208 are illustrated), alignable with the at least one surface directing projection 158; or at least one interface directing color marking 210 (e.g., FIG. 23; as an example, two interface directing color markings 210 are illustrated), alignable with the at least one surface directing color marking 170.

Referring, e.g., to FIGS. 17 and 21, as one example, the interface directional alignment feature 204 includes a plurality of interface directing projections 230 (e.g., FIG. 21) selectively alignable with the plurality of surface directing depressions 166 (e.g., FIG. 17). In one example implementation of the present disclosure, at least one interface directing projection 206 may correspond to at least one surface directing depression 164. As one example, the dimension 228 (e.g., FIG. 21) of at least one interface directing projection 206 may be suitably sized to mate with the dimension 168 (e.g., FIG. 17) of at least one surface directing depression 164. As one example, the dimensions 228 of each interface directing projection 206 may be defined as a cross-sectional dimension of the interface directing projection 206.

In one example, corresponding dimensions 228 of at least one interface directing projection 206 of the plurality of interface directing projections 230 and at least one other interface directing projection 206 of the plurality of interface directing projections 230 are different. In one example, corresponding dimensions 228 of all interface directing projections 206 of the plurality of interface directing projections 230 are different. As a result, the optical guide 190 (e.g., FIG. 21) may be repeatably positioned with respect to the surface 104 and/or the hydrophilic portion 108 (e.g., FIG. 17) such that the first incident non-destructive electromagnetic beam 114 (e.g., FIGS. 8 and 9) is consistently directed at the first directional orientation 224 (FIG. 17).

Referring to FIGS. 16 and 22, as one example, the interface directional alignment feature 204 includes a plurality of interface directing depressions 232 (e.g., FIG. 22) selectively alignable with the plurality of surface directing projections 160 (e.g., FIG. 16). In one example implementation of the present disclosure, at least one interface directing depression 208 may correspond to at least one surface directing projection 158. As one example, the dimension 236 (e.g., FIG. 22) of at least one interface directing depression 208 may be suitably sized to mate with the dimension 162 (e.g., FIG. 16) of at least one surface directing projection 158. As one example, the dimensions 236 of each interface directing depression 208 may be defined as a cross-sectional dimension of the interface directing depression 208.

In one example, corresponding dimensions 236 of at least one interface directing depression 208 of the plurality of interface directing depressions 232 and at least one other interface directing depression 208 of the plurality of interface directing depressions 232 are different. In one example, corresponding dimensions 236 of all interface directing projections 208 of the plurality of surface directing projections 232 are different. As a result, the optical guide 190 may be repeatably positioned with respect to the surface 104 and/or the hydrophilic portion 108 such that the first incident non-destructive electromagnetic beam 114 (e.g., FIGS. 8 and 9) is consistently directed at the first directional orientation 224.

Referring to FIGS. 18 and 23, as one example, the interface directional alignment feature 204 includes a plurality of interface directing color markings 234 selectively alignable with the plurality of surface directing color markings 172. In one example implementation of the present disclosure, at least one interface directing color marking 210 may correspond to at least one surface directing color marking 170. As one example, at least one interface directing depression 208 may match at least one surface directing color marking 170 (e.g., having the same shape, the same color, the same size or the like). Each directing color marking 210 of the plurality of surface directing color markings 234 may extend beyond the peripheral edge 258 of the interface surface, for example, the directing color marking 210 may extend from the peripheral edge 258 onto the housing 196 of the optical guide 190.

In one example, at least one interface directing color marking 210 of the plurality of surface directing color markings 234 is different than at least one other interface directing color marking 210 of the plurality of surface directing color markings 234. In one example, all interface directing color markings 210 of the plurality of interface directing color markings 234 are different. As a result, the optical guide 190 may be repeatably positioned with respect to the surface 104 and/or the hydrophilic portion 108 such that the first incident non-destructive electromagnetic beam 114 (e.g., FIGS. 8 and 9) is consistently directed at the first directional orientation 224.

Referring, e.g., to FIG. 24, in one aspect of the disclosure, which may include at least a portion of the subject matter of any of the preceding and/or following examples and aspects, the surface 104 includes additional hydrophilic portions 174. The hydrophilic portion 108 and the additional hydrophilic portions 174 form an arrangement 176 of hydrophilic portions.

Referring, e.g., to FIG. 24, in one aspect of the disclosure, which may include at least a portion of the subject matter of any of the preceding and/or following examples and aspects, the hydrophilic portions (i.e., the hydrophilic portion 108 and the additional hydrophilic portions 174) of the arrangement 176 of hydrophilic portions are evenly spaced away from each other.

Referring, e.g., to FIG. 25, in one aspect of the disclosure, which may include at least a portion of the subject matter of any of the preceding and/or following examples and aspects, the surface 104 includes at least one of: a plurality 178 of identifying features; a plurality 180 of surface center alignment features; or a plurality 182 of surface directional alignment features. Each of the hydrophilic portions (i.e., the hydrophilic portion 108 and the additional hydrophilic portions 174) is associated with at least one of: the identifying feature 138 of the plurality 178 of identifying features; the surface center alignment feature 144 of the plurality 180 of surface center alignment features; or the surface directional alignment feature 156 of the plurality 182 of surface directional alignment features.

As one example, the hydrophilic portion 108 and each of the additional hydrophilic portions 174 is associated with a corresponding identifying feature 138 of the plurality 178 of identifying features. As one example, the hydrophilic portion 108 and each of the additional hydrophilic portions 174 is associated with a corresponding surface center alignment feature 144 of the plurality 180 of surface center alignment features. As one example, the hydrophilic portion 108 and each of the additional hydrophilic portions 174 is associated with a corresponding surface directional alignment feature 156 of the plurality 182 of surface directional alignment features.

Referring generally to FIGS. 1-25 and particularly to FIGS. 26A and 26B, one example of the present disclosure relates to a method 500 for analyzing the sample 212 located on the hydrophilic portion 108 of the surface 104. The method 500 includes directing the first incident non-destructive electromagnetic beam 114 through the sample 212 at the non-zero incidence angle 192 relative to the surface 104 (block 502) and analyzing the first reflected non-destructive electromagnetic beam 188 reflected from the hydrophilic portion 108 to obtain a first measurement 214 associated with at least one property 216 of the sample 212 (block 504).

Referring, e.g., to FIGS. 1A, 1B and 2, as one example, and as described herein above, the sample 212 may include a liquid solvent and the residue 102. The sample 212 may be deposited on the hydrophilic portion 108 as a liquid droplet. The hydrophilic portion 108, or the pattern of the arrangement of hydrophilic portions 176, may cause the liquid droplet of the sample 212 to center upon the hydrophilic portion 108 and avoid the surrounding hydrophobic portion 106.

The first measurement 214 associated with at least one property 216 of the sample 212 may include detailed chemical information about the identity of the residue 102. As one example, the at least one property 216 of the sample 212 (e.g., the residue 102) may include, but is not limited to, a component in the analyte, the composition of the analyte, and a concentration of the analyte.

Referring, e.g., to FIGS. 26A and 26B, in one aspect of the disclosure, which may include at least a portion of the subject matter of any of the preceding and/or following examples and aspects, the method 500 includes aligning the first incident non-destructive electromagnetic beam 114 with the center 148 of the hydrophilic portion 108 (block 506).

Referring, e.g., to FIGS. 26A and 26B, in one aspect of the disclosure, which may include at least a portion of the subject matter of any of the preceding and/or following examples and aspects, aligning the first incident non-destructive electromagnetic beam 114 with the center 148 of the hydrophilic portion 108 (block 506) includes aligning the interface center alignment feature 202 of the interface surface 198 of the optical guide 190 and the surface center alignment feature 144 of the surface 104 (block 508).

Referring, e.g., to FIGS. 26A and 26B, in one aspect of the disclosure, which may include at least a portion of the subject matter of any of the preceding and/or following examples and aspects, the method 500 includes directionally aligning the first incident non-destructive electromagnetic beam 114 with the hydrophilic portion 108 (block 510).

Referring, e.g., to FIGS. 26A and 26B, in one aspect of the disclosure, which may include at least a portion of the subject matter of any of the preceding and/or following examples and aspects, directionally aligning the first incident non-destructive electromagnetic beam 114 with the hydrophilic portion 108 (block 510) includes aligning the interface directional alignment feature 204 of the interface surface 198 of the optical guide 190 and the surface directional alignment feature 156 of the surface 104 (block 512).

In one example, directionally aligning the first incident non-destructive electromagnetic beam 114 with the hydrophilic portion 108 (block 510) includes aligning the interface directional alignment feature 204 of the interface surface 198 of the optical guide 190 and the surface directional alignment feature 156 of the surface 104 in a first directional orientation 224 (block 514).

Referring, e.g., to FIGS. 26A and 26B, in one aspect of the disclosure, which may include at least a portion of the subject matter of any of the preceding and/or following examples and aspects, the method 500 includes passing the first incident non-destructive electromagnetic beam 114 through the sample 212 (block 516) and passing the first reflected non-destructive electromagnetic beam 188 through the sample 212 (block 518).

Referring, e.g., to FIGS. 26A and 26B, in one aspect of the disclosure, which may include at least a portion of the subject matter of any of the preceding and/or following examples and aspects, the method 500 includes directing a second incident non-destructive electromagnetic beam 218 through the sample 212 at the non-zero incidence angle 192 (block 520), analyzing a second reflected non-destructive electromagnetic beam 220 reflected from the hydrophilic portion 108 to obtain a second measurement 222 associated with at least one property 216 of the sample 212 (block 522), and averaging the first measurement 214 and the second measurement 222 (block 524).

Referring, e.g., to FIGS. 26A and 26B, in one aspect of the disclosure, which may include at least a portion of the subject matter of any of the preceding and/or following examples and aspects, the method 500 includes aligning the first incident non-destructive electromagnetic beam 114 with the center 148 of the hydrophilic portion 108 (block 506); directionally aligning the first incident non-destructive electromagnetic beam 114 with the hydrophilic portion 108 at the first directional orientation (blocks 510 and 514); aligning the second incident non-destructive electromagnetic beam 218 with the center 148 of the hydrophilic portion 108 (block 526), and directionally aligning the second incident non-destructive electromagnetic beam 218 with the hydrophilic portion 108 at a second directional orientation 226 (block 528).

Accordingly, the disclosed apparatus 100 and method 500 may improve non-destructive analysis of materials and chemicals, for example, by improving the sensitivity of spectro-photometric analysis and allowing for easier handling of samples. Advantageously, the disclosed apparatus 100 and method 500 may allow for: (1) archiving spectroscopic analysis data (e.g., saving and archiving the physical residue 102 disposed on the hydrophilic portion 108 of the surface 104 of the plate 106), (2) performing multiple spectroscopic analysis of a single sample 212 (e.g., residue 102 disposed on the hydrophilic portion 108 of the surface 104 of the plate 106) at a consistent and predetermined directional orientation 224, such that the results of multiple spectroscopic analysis can be averaged, and (3) reducing the cost of multiple spectroscopic analysis by reusing the plates 106, if the residue 102 can be washed off without damaging or destroying the residue 102 and/or the hydrophilic portion 108, when the plate 116 is used in conjunction with non-destructive electromagnetic light (e.g., the first incident non-destructive electromagnetic beam 114).

The disclosure and drawing figure(s) describing the operations of the method(s) set forth herein should not be interpreted as necessarily determining a sequence in which the operations are to be performed. Rather, although one illustrative order is indicated, it is to be understood that the sequence of the operations may be modified when appropriate. Accordingly, certain operations may be performed in a different order or simultaneously. Additionally, in some aspects of the disclosure, not all operations described herein need be performed.

Examples of the disclosure may be described in the context of an aircraft manufacturing and service method 1100, as shown in FIG. 27, and an aircraft 1102, as shown in FIG. 28. During pre-production, illustrative method 1100 may include specification and design 1104 of the aircraft 1102 and material procurement 1106. During production, component and subassembly manufacturing 1108 and system integration 1110 of the aircraft 1102 take place. Thereafter, the aircraft 1102 may go through certification and delivery 1112 to be placed in service 1114. While in service by a customer, the aircraft 1102 is scheduled for routine maintenance and service 1116 (which may also include modification, reconfiguration, refurbishment, and so on).

Each of the processes of the illustrative method 1100 may be performed or carried out by a system integrator, a third party, and/or an operator (e.g., a customer). For the purposes of this description, a system integrator may include, without limitation, any number of aircraft manufacturers and major-system subcontractors; a third party may include, without limitation, any number of vendors, subcontractors, and suppliers; and an operator may be an airline, leasing company, military entity, service organization, and so on.

As shown in FIG. 28, the aircraft 1102 produced by the illustrative method 100 may include an airframe 1118 with a plurality of high-level systems 1120 and an interior 1122. Examples of high-level systems 1120 include one or more of a propulsion system 1124, an electrical system 1126, a hydraulic system 1128, and an environmental system 1130. Any number of other systems may be included. Although an aerospace example is shown, the principles of the invention may be applied to other industries, such as the automotive industry.

Apparatus and methods shown or described herein may be employed during any one or more of the stages of the manufacturing and service method 1100. For example, components or subassemblies corresponding to component and subassembly manufacturing 1108 may be fabricated or manufactured in a manner similar to components or subassemblies produced while the aircraft 1102 is in service. Also, one or more aspects of the apparatus, method, or combination thereof may be utilized during the production states 1108 and 1110, for example, by substantially expediting assembly of or reducing the cost of an aircraft 1102. Similarly, one or more aspects of the apparatus or method realizations, or a combination thereof, may be utilized, for example and without limitation, while the aircraft 1102 is in service, e.g., maintenance and service 1116.

Different examples and aspects of the apparatus and methods are disclosed herein that include a variety of components, features, and functionality. It should be understood that the various examples and aspects of the apparatus and methods disclosed herein may include any of the components, features, and functionality of any of the other examples and aspects of the apparatus and methods disclosed herein in any combination, and all of such possibilities are intended to be within the spirit and scope of the present disclosure.

Many modifications and other examples of the disclosure set forth herein will come to mind to one skilled in the art to which the disclosure pertains having the benefit of the teachings presented in the foregoing descriptions and the associated drawings.

Therefore, it is to be understood that the disclosure is not to be limited to the specific embodiments disclosed and that modifications and other embodiments are intended to be included within the scope of the appended claims. Moreover, although the foregoing descriptions and the associated drawings describe example embodiments in the context of certain illustrative combinations of elements and/or functions, it should be appreciated that different combinations of elements and/or functions may be provided by alternative implementations without departing from the scope of the appended claims.

What is claimed is:

1. An apparatus (100) for spectroscopic analysis of a sample (212) formed from a liquid solvent and a residue (102), the apparatus (100) comprising:
 means (184) for generating an incident non-destructive electromagnetic beam (114), wherein the incident non-destructive electromagnetic beam (114) comprises a width (112);
 a plate (116);
 a hydrophilic material (130), coupled to the plate (116); and
 a hydrophobic substrate (132), coupled to the hydrophilic material (130); and wherein:
  the hydrophilic material (130) and the hydrophobic substrate (132) define a surface (104),
  the surface (104) comprises a hydrophobic portion (106) and a hydrophilic portion (108),
  the hydrophobic portion (106) of the surface (104) is defined by an absence of the hydrophilic material (130), the hydrophilic portion (108) of the surface (104) is defined by an absence of the hydrophobic substrate (132) and has a center (148), the hydrophilic portion (108) of the surface (104) is optically reflective, the hydrophobic portion (106) of the surface (104) surrounds the hydrophilic portion (108) of the surface (104), and the hydrophilic portion (108) of the surface (104) comprises a dimension (110), in plan view, equal to or larger than the width (112) of the incident non-destructive electromagnetic beam (114) directed at the hydrophilic portion (108) of the surface (104), passing through the sample (212) deposited on the hydrophilic portion (108) of the surface (104), and optically reflected from the hydrophilic portion (108) of the surface (104).

2. The apparatus (100) of claim 1, wherein the plate (116) comprises a metallic body (118).

3. The apparatus (100) of claim 1, wherein the plate (116) comprises a plastic body (120) and a metal coating (122) at least partially covering the plastic body (120).

4. The apparatus (100) of claim 1, wherein the surface (104) further comprises an identifying feature (138) associated with the hydrophilic portion (108).

5. The apparatus (100) of claim 4, wherein the identifying feature (138) is a visually identifiable boundary (140) between the hydrophilic portion (108) and the hydrophobic portion (106).

6. The apparatus (100) of claim 5, wherein the visually identifiable boundary (140) comprises an identifying color marking (142).

7. The apparatus of claim 1, wherein the surface further comprises a surface center alignment feature.

8. The apparatus of claim 7, wherein:
the hydrophilic portion further comprises a peripheral boundary and a center circumscribed by the peripheral boundary, and
the surface center alignment feature is concentric with the center of the hydrophilic portion and at least partially surrounds the peripheral boundary of the hydrophilic portion.

9. The apparatus of claim 8, wherein the surface center alignment feature is spaced away from the peripheral boundary of the hydrophilic portion.

10. The apparatus of claim 7, wherein the surface further comprises a surface directional alignment feature.

11. The apparatus of claim 10, wherein the surface directional alignment feature is at least partially coextensive with the surface center alignment feature.

12. The apparatus of claim 10, wherein:
the hydrophilic portion further comprises a center, and
the surface directional alignment feature is outward of the surface center alignment feature relative to the center of the hydrophilic portion.

13. The apparatus of claim 10, wherein:
the surface directional alignment feature comprises a plurality of surface directing projections, and
corresponding dimensions of at least one surface directing projection of the plurality of surface directing projections and at least one other surface directing projection of the plurality of surface directing projections are different.

14. The apparatus of claim 10, wherein:
the surface directional alignment feature comprises a plurality of surface directing projections, and
corresponding dimensions of all surface directing projections of the plurality of surface directing projections are different.

15. The apparatus of claim 10, wherein:
the surface directional alignment feature comprises a plurality of surface directing depressions, and
corresponding dimensions of at least one surface directing depression of the plurality of surface directing depressions and at least one other surface directing depression of the plurality of surface directing depressions are different.

16. The apparatus of claim 10, wherein:
the surface directional alignment feature comprises a plurality of surface directing depressions, and
corresponding dimensions of all surface directing depressions of the plurality of surface directing depressions are different.

17. The apparatus of claim 1, wherein:
the surface further comprises additional hydrophilic portions, and
the hydrophilic portion and the additional hydrophilic portions form an arrangement of hydrophilic portions.

18. The apparatus of claim 17, wherein hydrophilic portions of the arrangement of hydrophilic portions are evenly spaced away from each other.

19. The apparatus of claim 17, wherein:
the surface further includes at least one of a plurality of identifying features, a plurality of surface center alignment features, or a plurality of surface directional alignment features, and
each of the hydrophilic portions is associated with at least one of an identifying feature of the plurality of identifying features, a surface center alignment feature of the plurality of surface center alignment features, or a surface directional alignment feature of the plurality of surface directional alignment features.

20. The apparatus of claim 1, further comprising:
means for detecting a reflected non-destructive electromagnetic beam; and
an optical guide selectively optically coupled with the means for generating the incident non-destructive electromagnetic beam and the means for detecting the reflected non-destructive electromagnetic beam,
wherein the optical guide is selectively positioned in contact with the surface adjacent the hydrophilic portion.

21. The apparatus of claim 20, wherein:
the optical guide selectively directs the incident non-destructive electromagnetic beam at the hydrophilic portion at a non-zero incidence angle, and
the optical guide receives the reflected non-destructive electromagnetic beam at a non-zero reflective angle.

22. The apparatus of claim 21, wherein the incidence angle and the reflective angle are between 5 degrees and 20 degrees.

23. The apparatus of claim 20, wherein the optical guide comprises:
a housing comprising an interface surface; and
a lens inside the housing.

24. The apparatus of claim 23, wherein:
the surface further comprises a surface center alignment feature, and
the interface surface comprises an interface center alignment feature corresponding to the surface center alignment feature.

25. The apparatus of claim 24, wherein:
the hydrophilic portion further comprises a peripheral boundary and a center circumscribed by the peripheral boundary,
the surface center alignment feature is concentric with the center of the hydrophilic portion and at least partially surrounds the peripheral boundary of the hydrophilic portion,
the interface center alignment feature is alignable with the surface center alignment feature.

26. The apparatus of claim 24, wherein:
the surface further comprises a surface directional alignment feature, and
the interface surface further comprises an interface directional alignment feature corresponding to the surface directional alignment feature.

27. The apparatus of claim 26, wherein:
the surface directional alignment feature comprises at least one of:
  at least one surface directing projection;
  at least one surface directing depression; or
  at least one surface directing color marking, and
the interface directional alignment feature comprises at least one of:
  at least one interface directing projection alignable with the at least one surface directing depression;
  at least one interface directing depression alignable with the at least one surface directing projection; or
  at least one interface directing color marking alignable with the at least one surface directing color marking.

28. The apparatus (100) of claim 1, wherein:
the dimension (110), in plan view, of the hydrophilic portion (108) of the surface (104) is at least 5 millimeters,
the hydrophobic substrate (132) comprises a thickness (240) of at most 50 nanometers, and
when the incident non-destructive electromagnetic beam (114), having an incident angle (192) of at most 20 degrees relative to the hydrophilic portion (108) of the surface (104), is directed at the center (148) of the hydrophilic portion (108), the incident non-destructive electromagnetic bean (114) is not obstructed by the hydrophobic portion (106) of the surface (104).

* * * * *